(12) United States Patent
Zhang et al.

(10) Patent No.: US 7,393,869 B2
(45) Date of Patent: Jul. 1, 2008

(54) METHODS OF USING THIAZOLIDINE DERIVATIVES TO TREAT CANCER OR INFLAMMATION

(75) Inventors: Zaihui Zhang, Vancouver (CA); Timothy S. Daynard, Vancouver (CA); Gabriel Bela Kalmar, Richmond (CA)

(73) Assignee: QLT Inc., Vancouver, BC (CA)

( * ) Notice: Subject to any disclaimer, the term of this patent is extended or adjusted under 35 U.S.C. 154(b) by 0 days.

(21) Appl. No.: 10/514,174

(22) PCT Filed: May 8, 2003

(86) PCT No.: PCT/CA03/00682

§ 371 (c)(1), (2), (4) Date: Jul. 7, 2005

(87) PCT Pub. No.: WO03/094916

PCT Pub. Date: Nov. 20, 2003

(65) Prior Publication Data

US 2006/0183782 A1 Aug. 17, 2006

Related U.S. Application Data

(60) Provisional application No. 60/379,929, filed on May 10, 2002.

(51) Int. Cl.
*A01N 43/82* (2006.01)
*A61K 31/535* (2006.01)
(52) U.S. Cl. .................................. 514/361; 514/236.2
(58) Field of Classification Search ................ 514/361
See application file for complete search history.

(56) References Cited

U.S. PATENT DOCUMENTS

| | | | |
|---|---|---|---|
| 4,464,382 A | 8/1984 | Tanouchi et al. | 424/270 |
| 4,791,126 A | 12/1988 | Tanouchi et al. | 514/369 |
| 4,831,045 A | 5/1989 | Tanouchi et al. | 514/369 |
| 4,965,155 A | 10/1990 | Nishiguchi et al. | 430/58 |
| 5,227,473 A * | 7/1993 | Kawamura et al. | 534/557 |
| 5,310,618 A | 5/1994 | Kawamura | 430/157 |
| 5,691,367 A | 11/1997 | Panetta | 514/369 |
| 5,726,027 A | 3/1998 | Olefsky | 435/7.21 |
| 6,262,044 B1 | 7/2001 | Møller et al. | 514/202 |
| 6,727,268 B2 * | 4/2004 | Cho et al. | 514/369 |

FOREIGN PATENT DOCUMENTS

| | | |
|---|---|---|
| EP | 0047109 A1 | 3/1982 |
| JP | 01147472 | 6/1989 |
| JP | 01172835 | 7/1989 |
| JP | 01172836 | 7/1989 |
| JP | 01173064 | 7/1989 |
| WO | WO 99/43664 | 9/1999 |
| WO | WO 99/61467 | 12/1999 |
| WO | WO 00/36111 | 6/2000 |
| WO | WO 00/76988 | 12/2000 |
| WO | WO 01/57006 | 8/2001 |

OTHER PUBLICATIONS

Gorishnyi et al. Farm.ZH. 1995 (4) 50-53.*
Gura (Science, 1997, 278:1041-1042).*
Jain (Sci. Am., 1994, 271:58-65).*
Curti (Crit. Rev. in Oncology/Hematology, 1993, 14:29-39).*
Ahmad, F., et al. "Alterations in skeletal muscle protein-tyrosine phosphatase activity and expression in insulin-resistant human obesity and diabetes" J Clin Invest (Jul. 1997) 100(2):449-458.
Cool, D.E., et al., "cDNA isolated from a human T-cell library encodes a member of the protein-tyrosine-phosphatase family" PNAS USA (Jul. 1989) 86(14):5257-61.
Davidson, D., et al. "PTP-PEST, a scaffold protein tyrosine phosphatase, negatively regulates lymphocyte activation by targeting a unique set of substrates" EMBO J (2001) 20(13):3414-26.
Elchebly, M. et al. "Increased insulin sensitivity and obesity resistance in mice lacking the protein tyrosine phosphatase-1B gene" Science (Mar. 1999) 283(5407): 1544-8.
Galic, S. et al. Regulation of insulin receptor signaling by the protein tyrosine phosphatase TCPTP Mol. Cell. Biol. (Mar. 2003) 23(6): 2096-2108.
Garton, A.J., et al. "Regulation of fibroblast motility by the protein tyrosine phosphatase PTP-PEST" J Biol Chem (Feb. 1999) 274(6):3811-3818.
Gorishnii, V. Ya, et al. "Synthesis and properties of rodanine carboxyamides" Farmatsevtichnii Zhurnal (Kiev) (2001) 2:64-67.
Gorishnyi, V. Ya, et al. "Synthesis and antiphlogistic activity of 5-aryledenerhodanin-3-alkynoic acid amides" Farmatsevtichnii Zhurnal (Kiev) (1995) 4:50-53.
Gum, R.J., Gaede, L.L., Koterski, S.L., et al. "Reduction of protein tyrosine phosphatase 1B increases insulin-dependent signaling in ob/ob mice" Diabetes (Jan. 2003) 52(1):21-28.
Ibarra-Sanchez, M.J., et al. "Murine embryonic fibroblasts lacking TC-PTP display delayed G1 phase through defective NF-kappaB activation" Oncogene (2001) 20(34):4728-39.

(Continued)

*Primary Examiner*—Ardin H. Marschel
*Assistant Examiner*—Shirley V Gembeh
(74) *Attorney, Agent, or Firm*—Seed IP Law Group PLLC

(57) ABSTRACT

Methods of using thiazolidine derivatives of formula (I) to treat cancer, inflammation, or other disorders related to the activities of protein phosphatases PTPN12 or PTPN2 in a mammal are disclosed. Pharmaceutical compositions containing such derivatives are disclosed

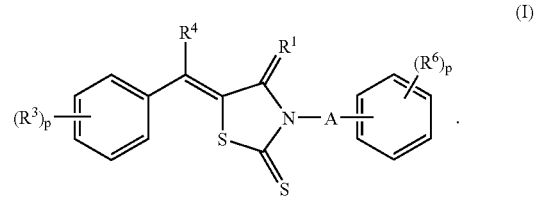

6 Claims, No Drawings

OTHER PUBLICATIONS

Mitra, S. K., et al. "Inhibition of anchorage-independent cell growth, adhesion, and cyclin D1 gene expression by a dominant negative mutant of a tyrosine phosphatase" Exp Cell Res (2001) 270(1):32-44.

Radha, V., et al. "Induction of p53 dependent apoptosis upon overexpression of a nuclear protein tyrosine phosphatase" FEBS Letters (1999) 453(3):308-312.

Reiser, J., et al. "Regulation of mouse podocyte process dynamic by protein tyrosine phosphatases rapid communication" Kidney Int (2000) 57(5):2035-2042.

Takekawa, M., et al. "Chromosomal localization of the protein tyrosine phosphatase G1 gene and characterization of he aberrant transcripts in human colon cancer cells" FEBS Letters (1994) 339(3):222-228.

Yang, Q. et al., "Cloning and Expression of PTP-PEST. A Novel, Human, Nontransmembrane Protein Tyrosine Phosphatase," *The Journal of Biological Chemistry* 268(9): 6622-6628, Mar. 25, 1998.

You-Ten, K.E., et al. "Impaired bone marrow microenvironment and immune function in T cell protein tyrosine phosphatase-deficient mice" J Exp Med (1997) 186(5):683-693.

* cited by examiner

METHODS OF USING THIAZOLIDINE DERIVATIVES TO TREAT CANCER OR INFLAMMATION

CROSS REFERENCE TO RELATED APPLICATIONS

This application is a national stage application filed under 35 U.S.C. 371 of International Application No. PCT/CA03/000682, accorded an International Filing Date of May 8, 2003, which claims priority to U.S. Provisional Patent Application No. 60/379,929, filed May 10, 2002, where these applications are incorporated herein by reference in their entireties.

FIELD OF THE INVENTION

This invention is directed to methods of using thiazolidine derivatives to treat cancer or inflammation in a mammal.

BACKGROUND OF THE INVENTION

Protein tyrosine phosphorylation is an important mechanism for transmitting extracellular stimuli in biochemical and cellular events such as cell attachment, mitogenesis, differentiation and migration (see e.g., Li, Liwu et al., *Seminars in Immunology* (2000), Vol. 12, pp. 75-84, and Neel, B. G. et al., *Current Opinion in Cell Biology* (1997), Vol. 9, pp. 193-204). Kinases and phosphatases are enzymes that help regulate many cellular activities, particularly signaling from the cell membrane to the nucleus to initiate the cell's entrance into the cell cycle and to control other functions.

Phosphorylation is important in signal transduction mediated by receptors via extracellular biological signals such as growth factors or hormones. For example, many oncogenes are kinases or phosphatases, i.e. enzymes that catalyze protein phosphorylation or dephosphorylation reactions or are specifically regulated by phosphorylation. In addition, a kinase or phosphatase can have its activity regulated by one or more distinct kinase or phosphatases, resulting in specific signaling cascades.

All protein tyrosine phosphatases (PTPs) have a conserved catalytic domain characterized by a signature sequence (I/V)HCXXGXX(S/T) (SEQ ID NO: 1). Biochemical and kinetic studies have demonstrated that the cysteine residue found in this signature sequence is essential for catalytic activity of PTPs since this mutation of this cysteine completely abolishes PTP activity. See, Flint, A. J., et al., *Proceedings of the National Academy of Sciences of the United States of America* 94 (1997), pp. 1680-1685.

DESCRIPTION OF THE RELATED ART

PCT Published Patent Application, WO 99/61467 (McGill University), describes agents that interfere with the binding of PTPN12 (PTP-PEST) to domains of signalling proteins as inhibitors of cell migration and/or of focal adhesion.

PCT Published Patent Application, WO 00/36111 (McGill University) describes methods of utilizing PTPN2 (TC-PTP) for screening.

U.S. Pat. No. 5,726,027 by Olefsky, Jerrold M. describes a screening method for identifying compositions which affect the binding of protein tyrosine phosphatase 1B (PTP1B).

U.S. Pat. No. 6,262,044 (Novo Nordisk) describes certain protein tyrosine phosphatase inhibitors and provides a detailed description of the discovery of protein tyrosine phosphatases and their pathophysiological roles.

Gorishni, V. Ya. et al, *Farm. Zh. (Kiev)* (2001), Vol. 2, pp. 64-67, and Gorishnyi, V. Ya. et al, *Farm. Zh. (Kiev)* (1995), Vol. 4, pp. 50-53, discloses 4-oxo-2-thioxothiazolidine derivatives useful in treating inflammation.

PCT Published Patent Application WO 00/76988 (Warner-Lambert) discloses 4-oxo-2-thioxothiazolidine derivatives useful as amyloid aggregation inhibitors and in imaging amyloid deposits.

European Patent Specification 0047109 (Ono Pharmaceuticals) discloses 4-oxo-2-thioxothiazolidine derivatives useful in inhibiting aldose reductase.

SUMMARY OF THE INVENTION

This invention is directed to the use of certain thiazolidine derivatives in treating cancer and inflammation in a mammal.

Accordingly, one aspect of this invention provides a method of treating cancer in a mammal, which method comprises administering to the mammal in need thereof a therapeutically effective amount of a compound of formula (I):

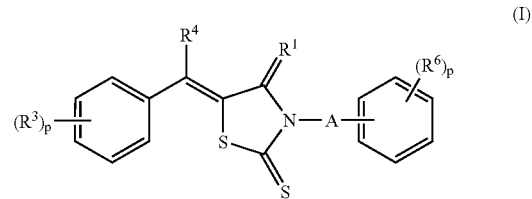

wherein:

each p is independently 1 to 5;

A is a linker of four atoms and is selected from the group consisting of an optionally substituted straight or branched alkylene chain of four carbons, an optionally substituted straight or branched alkenylene chain of four carbons, —$R^8$—C($R^2$)—N($R^5$)—, —$R^8$—N($R^5$)—C($R^2$)—, —$R^8$—O—C($R^2$)—, —$R^7$—O—C($R^2$)—$R^7$—, —$R^8$—O—$R^7$—, —$R^7$—C($R^2$)—N($R^5$)—S(O)$_t$— (where t is 0 to 2), —$R^8$—N($R^5$)—$R^7$—, —$R^8$—S(O)$_t$—$R^7$— (where t is 0 to 2), —$R^9$—N($R^5$)—, —$R^9$—O—, and —$R^9$—C($R^2$)—;

$R^1$ and $R^2$ are each independently =O or =S;

each $R^3$ and $R^6$ are independently selected from the group consisting of hydrogen, alkyl, alkenyl, aryl, aralkyl, aralkenyl, cycloalkyl, cycloalkylalkyl, halo, haloalkyl, haloalkoxy, nitro, cyano, —N=N—O—$R^{11}$, —O$R^{10}$, —C(O)O$R^{10}$, —C(O)N($R^{10}$)$_2$, —N($R^{10}$)$_2$, —N($R^{10}$)C(O)$R^{10}$, —N($R^{10}$)C(O)O$R^{11}$, —S(O)$_t$$R^{10}$ (where t is 0 to 2), —S(O)$_t$N($R^{10}$)$_2$ (where t is 0 to 2), —S(O)$_t$NH—$R^{14}$, heterocyclyl and heterocyclylalkyl;

$R^4$ is hydrogen, alkyl, aralkyl, aryl, haloalkyl, cycloalkyl, cycloalkylalkyl, heterocyclyl or heterocyclylalkyl;

each $R^5$ is independently hydrogen, alkyl, aralkyl, or aryl;

each $R^7$ is an optionally substituted alkylene chain of one carbon;

each $R^8$ is an optionally substituted straight or branched alkylene or alkenylene chain of two carbons;

each $R^9$ is an optionally substituted alkylene chain of three carbons;

each $R^{10}$ is hydrogen, alkyl, alkenyl, cycloalkyl, cycloalkylalkyl, aralkyl or aryl; and $R^{11}$ is hydrogen, alkyl or aralkyl;

$R^{14}$ is a thiazole;

as a single stereoisomer, a mixture of stereoisomers, or as a racemic mixture of stereoisomers; or as a solvate or polymorph; or as a pharmaceutically acceptable salt thereof.

In another aspect, this invention provides a method of treating inflammation in a mammal, which method comprises administering to the mammal in need thereof a therapeutically effective amount of a compound of formula (Ia):

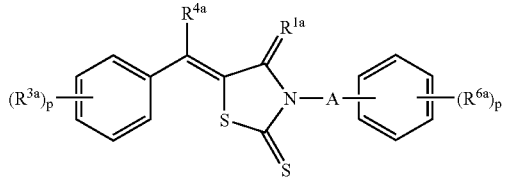

(Ia)

wherein:

each p is independently 1 to 5;

A is linker of four atoms and is selected from the group consisting of an optionally substituted straight or branched alkylene chain of four carbons, an optionally substituted straight or branched alkenylene chain of four carbons, $-R^{8a}-C(R^{2a})-N(R^{5a})-$, $-R^{8a}-N(R^{5a})-C(R^{2a})-$, $-R^{8a}-O-C(R^{2a})-$, $-R^{7a}-O-C(R^{2a})-R^{7a}-$, $-R^{8a}-O-R^{7a}-$, $-R^{7a}-C(R^{2a})-N(R^{5a})-S(O)_t-$ (where t is 0 to 2), $-R^{8a}-N(R^{5a})-R^{7a}-$, $-R^{8a}-S(O)_t-R^{7a}-$ (where t is 0 to 2), $-R^{9a}-N(R^{5a})-$, $-R^{9a}-O-$, and $-R^{9a}-C(R^{2a})-$;

$R^{1a}$ and $R^{2a}$ are each independently =O or =S;

$R^{3a}$ is alkyl, alkenyl, aryl, aralkyl, aralkenyl, cycloalkyl, cycloalkylalkyl, chloro, iodo, bromo, haloalkyl, haloalkoxy, nitro, cyano, $-N=N-O-R^{11a}$, $-OR^{10a}$, $-C(O)OR^{10a}$, $-C(O)N(R^{10a})_2$, $-N(R^{12a})_2$, $-N(R^{10a})C(O)R^{10a}$, $-N(R^{10a})C(O)OR^{11a}$, $-S(O)_tR^{10a}$ (where t is 0 to 2), '$S(O)_t$N(R^{10a})_2$ (where t is 0 to 2), or heterocyclylalkyl;

$R^{4a}$ is hydrogen, alkyl, aralkyl, aryl, haloalkyl, cycloalkyl, cycloalkylalkyl, heterocyclyl or heterocyclylalkyl;

$R^{5a}$ is hydrogen, alkyl, aralkyl, or aryl;

$R^{6a}$ is alkyl, alkenyl, aryl, aralkyl, aralkenyl, cycloalkyl, cycloalkylalkyl, halo, haloalkyl, haloalkoxy, nitro, cyano, $-N=N-O-R^{11a}$, $-C(O)N(R^{10a})_2$, $-N(R^{10a})_2$, $-N(R^{10a})C(O)R^{10a}$, $-N(R^{10a})C(O)OR^{11a}$, $-S(O)_tR^{10a}$ (where t is 0 to 2), $-S(O)_tN(R^{10a})_2$ (where t is 0 to 2), $-S(O)_tNH-R^{14a}$, heterocyclyl or heterocyclylalkyl;

each $R^{7a}$ is an optionally substituted alkylene chain of one carbon;

each $R^{8a}$ is an optionally substituted straight or branched alkylene or alkenylene chain of two carbons;

each $R^{9a}$ is an optionally substituted alkylene chain of three carbons;

each $R^{10a}$ is hydrogen, alkyl, alkenyl, cycloalkyl, cycloalkylalkyl, aralkyl or aryl;

$R^{11a}$ is hydrogen, alkyl or aralkyl; and $R^{12a}$ is hydrogen, aryl or aralkyl;

$R^{14a}$ is a thiazole;

as a single stereoisomer, a mixture of stereoisomers, or as a racemic mixture of stereoisomers; or as a solvate or polymorph; or as a pharmaceutically acceptable salt thereof.

In another aspect, this invention provides a method of treating a mammal having a disorder or condition associated with hyperproliferation and tissue remodelling or repair, wherein said method comprises administering to the mammal having the disorder or condition a therapeutically effective amount of a compound of formula (I):

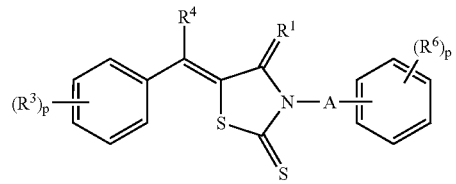

(I)

wherein:

each p is independently 1 to 5;

A is a linker of four atoms and is selected from the group consisting of an optionally substituted straight or branched alkylene chain of four carbons, an optionally substituted straight or branched alkenylene chain of four carbons, $-R^8-C(R^2)-N(R^5)-$, $-R^8-N(R^5)-C(R^2)-$, $-R^8-O-C(R^2)-$, $-R^7-O-C(R^2)-R^7-$, $-R^8-O-R^7-$, $-R^7-C(R^2)-N(R^5)-S(O)_t-$ (where t is 0 to 2), $-R^8-N(R^5)-R^7-$, $-R^8-S(O)_t-R^7-$ (where t is 0 to 2), $-R^9-N(R^5)-$, $-R^9-O-$, and $-R^9-C(R^2)-$;

$R^1$ and $R^2$ are each independently =O or =S;

each $R^3$ and $R^6$ are independently selected from the group consisting of hydrogen, alkyl, alkenyl, aryl, aralkyl, aralkenyl, cycloalkyl, cycloalkylalkyl, halo, haloalkyl, haloalkoxy, nitro, cyano, $-N=N-O-R^{11}$, $-OR^{10}$, $-C(O)OR^{10}$, $-C(O)N(R^{10})_2$, $-N(R^{10})_2$, $-N(R^{10})C(O)R^{10}$, $-N(R^{10})C(O)OR^{11}$, $-S(O)_tR^{10}$ (where t is 0 to 2), $-S(O)_tN(R^{10})_2$ (where t is 0 to 2), heterocyclyl and heterocyclylalkyl;

$R^4$ is hydrogen, alkyl, aralkyl, aryl, haloalkyl, cycloalkyl, cycloalkylalkyl, heterocyclyl or heterocyclylalkyl;

each $R^5$ is independently hydrogen, alkyl, aralkyl, or aryl;

each $R^7$ is an optionally substituted alkylene chain of one carbon;

each $R^8$ is an optionally substituted straight or branched alkylene or alkenylene chain of two carbons;

each $R^9$ is an optionally substituted alkylene chain of three carbons;

each $R^{10}$ is hydrogen, alkyl, alkenyl, cycloalkyl, cycloalkylalkyl, aralkyl or aryl; and $R^{11}$ is hydrogen, alkyl or aralkyl;

as a single stereoisomer, a mixture of stereoisomers, or as a racemic mixture of stereoisomers; or as a solvate or polymorph; or as a pharmaceutically acceptable salt thereof.

In another aspect, this invention provides a method of treating a mammalian cell with a compound of formula (I):

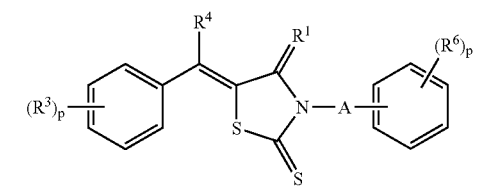

(I)

wherein:

each p is independently 1 to 5;

A is a linker of four atoms and is selected from the group consisting of an optionally substituted straight or branched alkylene chain of four carbons, an optionally substituted straight or branched alkenylene chain of four carbons, $-R^8-C(R^2)-N(R^5)-$, $-R^8-N(R^5)-C(R^2)-$, $-R^8-O-C(R^2)-$, $-R^7-O-C(R^2)-R^7-$, $-R^8-O-R^7-$, —R⁷—C(R²)—N(R⁵)—S(O)$_t$— (where t is 0 to 2), —R⁸—N(R⁵)—R⁷, —R⁸—S(O)$_t$—R⁷— (where t is 0 to 2), —R⁹—N(R⁵)—, —R⁹—O—, and —R⁹—C(R²)—;

R¹ and R² are each independently =O or =S;

each R³ and R⁶ are independently selected from the group consisting of hydrogen, alkyl, alkenyl, aryl, aralkyl, aralkenyl, cycloalkyl, cycloalkylalkyl, halo, haloalkyl, haloalkoxy, nitro, cyano, —N=N—O—R¹¹, —OR¹⁰, —C(O)OR¹⁰, —C(O)N(R¹⁰)₂, —N(R¹⁰)₂, —N(R¹⁰)C(O)R¹⁰, —N(R¹⁰)C(O)OR¹¹, —S(O)$_t$R¹⁰ (where t is 0 to 2), —S(O)$_t$N(R¹⁰)₂ (where t is 0 to 2), heterocyclyl and heterocyclylalkyl;

R⁴ is hydrogen, alkyl, aralkyl, aryl, haloalkyl, cycloalkyl, cycloalkylalkyl, heterocyclyl or heterocyclylalkyl;

each R⁵ is independently hydrogen, alkyl, aralkyl, or aryl;

each R⁷ is an optionally substituted alkylene chain of one carbon;

each R⁸ is an optionally substituted straight or branched alkylene or alkenylene chain of two carbons;

each R⁹ is an optionally substituted alkylene chain of three carbons;

each R¹⁰ is hydrogen, alkyl, alkenyl, cycloalkyl, cycloalkylalkyl, aralkyl or aryl; and R¹¹ is hydrogen, alkyl or aralkyl;

as a single stereoisomer, a mixture of stereoisomers, or as a racemic mixture of stereoisomers; or as a solvate or polymorph; or as a pharmaceutically acceptable salt thereof;

wherein the method comprises administering the compound of formula (I) to a mammalian cell and the compound of formula (I) is capable of inhibiting the activity of PTPN12, PTPN2, and/or PTPN1 within the mammalian cell.

In another aspect, this invention provides a pharmaceutical composition useful in treating cancer or inflammation in a human, wherein the pharmaceutical composition comprises a pharmaceutically acceptable carrier, diluent or excipient and a compound of formula (Ia):

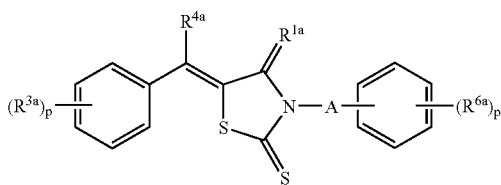

(Ia)

wherein:

each p is independently 1 to 5;

A is linker of four atoms and is selected from the group consisting of an optionally substituted straight or branched alkylene chain of four carbons, an optionally substituted straight or branched alkenylene chain of four carbons, —R⁸ᵃ—C(R²ᵃ)—N(R⁵ᵃ)—, —R⁸ᵃ—N(R⁵ᵃ)—C(R²ᵃ)—, —R⁸ᵃ—O—C(R²ᵃ)—, —R⁷ᵃ—O—C(R²ᵃ)—R⁷ᵃ—, —R⁸ᵃ—O—R⁷ᵃ—, —R⁷ᵃ—C(R²ᵃ)—N(R⁵ᵃ)—S(O)$_t$— (where t is 0 to 2), —R⁸ᵃ—N(R⁵ᵃ)—R⁷ᵃ, —R⁸ᵃ—S(O)$_t$—R⁷ᵃ— (where t is 0 to 2), —R⁹ᵃ—N(R⁵ᵃ)—, —R⁹ᵃ—O—, and —R⁹ᵃ—C(R²ᵃ)—;

R¹ᵃ and R²ᵃ are each independently =O or =S;

R³ᵃ is alkyl, alkenyl, aryl, aralkyl, aralkenyl, cycloalkyl, cycloalkylalkyl, chloro, iodo, bromo, haloalkyl, haloalkoxy, nitro, cyano, —N=N—O—R¹¹ᵃ, —OR¹⁰ᵃ, —C(O)OR¹⁰ᵃ, —C(O)N(R¹⁰ᵃ)₂, —N(R¹²ᵃ)₂, —N(R¹⁰ᵃ)C(O)R¹⁰ᵃ, —N(R¹⁰ᵃ)C(O)OR¹¹ᵃ, —S(O)$_t$R¹⁰ᵃ (where t is 0 to 2), —S(O)$_t$N(R¹⁰ᵃ)₂ (where t is 0 to 2), or heterocyclylalkyl;

R⁴ᵃ is hydrogen, alkyl, aralkyl, aryl, haloalkyl, cycloalkyl, cycloalkylalkyl, heterocyclyl or heterocyclylalkyl;

R⁵ᵃ is hydrogen, alkyl, aralkyl, or aryl;

R⁶ᵃ is alkyl, alkenyl, aryl, aralkyl, aralkenyl, cycloalkyl, cycloalkylalkyl, halo, haloalkyl, haloalkoxy, nitro, cyano, —N=N—O—R¹¹ᵃ, —C(O)N(R¹⁰ᵃ)₂, —N(R¹⁰ᵃ)₂, —N(R¹⁰ᵃ)C(O)R¹⁰ᵃ, —N(R¹⁰ᵃ)C(O)OR¹¹ᵃ, —S(O)$_t$R¹⁰ᵃ (where t is 0 to 2), —S(O)$_t$N(R¹⁰ᵃ)₂ (where t is 0 to 2), heterocyclyl or heterocyclylalkyl;

each R⁷ᵃ is an optionally substituted alkylene chain of one carbon;

each R⁸ᵃ is an optionally substituted straight or branched alkylene or alkenylene chain of two carbons;

each R⁹ᵃ is an optionally substituted alkylene chain of three carbons;

each R¹⁰ᵃ is hydrogen, alkyl, alkenyl, cycloalkyl, cycloalkylalkyl, aralkyl or aryl;

R¹¹ᵃ is hydrogen, alkyl or aralkyl; and

R¹²ᵃ is hydrogen, aryl or aralkyl;

as a single stereoisomer, a mixture of stereoisomers, or as a racemic mixture of stereoisomers; or as a solvate or polymorph; or as a pharmaceutically acceptable salt thereof.

In another aspect of the invention, the use of pharmaceutical compositions of the invention for the treatment of cancer or inflammation in provided.

In another aspect of the invention, the use of pharmaceutical compositions are provided for use in treating colon or colorectal cancer.

In another aspect of the invention, the use of pharmaceutical compositions of the invention in the manufacture of medicaments for the treatment of cancer and/or inflammation are provided.

In another aspect of the invention, the use of pharmaceutical compositions are provided for the treatment of disorders associated with hyperproliferation, tissue remodeling, and/or tissue repair.

In another aspect of the invention, the use of pharmaceutical compositions are provided for the treatment of endocrine disorders.

In another aspect of the invention, the use of pharmaceutical compositions are provided for the treatment of disorders associated with PTPN12, PTPN2, and/or PTPN1 expression.

DETAILED DESCRIPTION OF THE INVENTION

Definitions

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art. As used in the specification and appended claims, unless specified to the contrary, the following terms have the meaning indicated.

"Alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl(isopropyl), n-butyl, n-pentyl, 1,1-dimethylethyl(t-butyl), and the like. Unless stated otherwise specifically in the specification, the alkyl radical may be optionally substituted by hydroxy, alkoxy, aryloxy, haloalkoxy, cyano, nitro, mercapto, alkylthio, —N(R⁸)₂, —C(O)OR⁸, —C(O)N(R⁸)₂ or —N(R⁸)C(O)R⁸ where each R⁸ is independently hydrogen, alkyl, alkenyl, cycloalkyl, cycloalkylalkyl, aralkyl or aryl. Unless stated otherwise specifically in the specification, it is understood that for radicals, as defined below, that contain a substituted alkyl group that the substitution can occur on any carbon of the alkyl group.

"Alkoxy" refers to a radical of the formula —OR$_a$ where R$_a$ is an alkyl radical as defined above, e.g., methoxy, ethoxy, n-propoxy, 1-methylethoxy(iso-propoxy), n-butoxy, n-pentoxy, 1,1-dimethylethoxy(t-butoxy), and the like. Unless stated otherwise specifically in the specification, it is understood that for radicals, as defined below, that contain a substituted alkoxy group that the substitution can occur on any carbon of the alkoxy group. The alkyl radical in the alkoxy radical may be optionally substituted as described above.

"Alkylthio" refers to a radical of the formula —SR$_a$ where R$_a$ is an alkyl radical as defined above, e.g., methylthio, ethylthio, n-propylthio, 1-methylethylthio(iso-propylthio), n-butylthio, n-pentylthio, 1,1-dimethylethylthio(t-butylthio), and the like. Unless stated otherwise specifically in the specification, it is understood that for radicals, as defined below, that contain a substituted alkylthio group that the substitution can occur on any carbon of the alkylthio group. The alkyl radical in the alkylthio radical may be optionally substituted as described above.

"Alkenyl" refers to a straight or branched hydrocarbon chain radical consisting solely of carbon and hydrogen atoms, containing at least one double bond, having from two to eight carbon atoms, and which is attached to the rest of the molecule by a single bond or a double bond, e.g., ethenyl, prop-1-enyl, but-1-enyl, pent-1-enyl, penta-1,4-dienyl, and the like. Unless stated otherwise specifically in the specification, the alkenyl radical may be optionally substituted by hydroxy, alkoxy, haloalkoxy, cyano, nitro, mercapto, alkylthio, cycloalkyl, —N(R$^8$)$_2$, —C(O)OR$^8$, —C(O)N(R$^8$)$_2$ or —N(R$^8$)—C(O)—R$^8$ where each R$^8$ is independently hydrogen, alkyl, alkenyl, cycloalkyl, cycloalkylalkyl, aralkyl or aryl. Unless stated otherwise specifically in the specification, it is understood that for radicals, as defined below, that contain a substituted alkenyl group that the substitution can occur on any carbon of the alkenyl group.

"Aryl" refers to a phenyl or naphthyl radical. Unless stated otherwise specifically in the specification, the term "aryl" or the prefix "ar-" (such as in "aralkyl") is meant to include aryl radicals optionally substituted by one or more substituents selected from the group consisting of hydroxy, alkoxy, aryloxy, haloalkoxy, cyano, nitro, mercapto, alkylthio, cycloalkyl, —N(R$^8$)$_2$, —C(O)OR$^8$, —C(O)N(R$^8$)$_2$ or —N(R$^8$)C(O)R$^8$ where each R$^8$ is independently hydrogen, alkyl, alkenyl, cycloalkyl, cycloalkylalkyl, aralkyl or aryl.

"Aralkyl" refers to a radical of the formula —R$_a$R$_b$ where R$_a$ is an alkyl radical as defined above and R$_b$ is one or more aryl radicals as defined above, e.g., benzyl, diphenylmethyl and the like. The aryl radical(s) may be optionally substituted as described above.

"Aralkenyl" refers to a radical of the formula —R$_c$R$_b$ where R$_c$ is an alkenyl radical as defined above and R$_b$ is one or more aryl radicals as defined above, e.g., 3-phenylprop-1-enyl, and the like. The aryl radical(s) and the alkenyl radical may be optionally substituted as described above.

"Alkylene chain" refers to a straight or branched divalent hydrocarbon chain consisting solely of carbon and hydrogen, containing no unsaturation and having from one to eight carbon atoms, e.g., methylene, ethylene, propylene, n-butylene, and the like. The alkylene chain may be optionally substituted by one or more substituents selected from the group consisting of aryl, halo, hydroxy, alkoxy, haloalkoxy, cyano, nitro, mercapto, alkylthio, cycloalkyl, —N(R$^8$)$_2$, —C(O)OR$^8$, —C(O)N(R$^8$)$_2$ or —N(R$^8$)C(O)R$^8$ where each R$^8$ is independently hydrogen, alkyl, alkenyl, cycloalkyl, cycloalkylalkyl, aralkyl or aryl. The alkylene chain may be attached to the rest of the molecule through any two carbons within the chain.

"Alkenylene chain" refers to a straight or branched divalent hydrocarbon chain consisting solely of carbon and hydrogen, containing at least one double bond and having from two to eight carbon atoms, e.g., ethenylene, prop-1-enylene, but-1-enylene, pent-1-enylene, hexa-1,4-dienylene, and the like. The alkenylene chain may be optionally substituted by one or more substituents selected from the group consisting of aryl, halo, hydroxy, alkoxy, haloalkoxy, cyano, nitro, mercapto, alkylthio, cycloalkyl, —N(R$^8$)$_2$, —C(O)OR$^8$, —C(O)N(R$^8$)$_2$ or —N(R$^8$)C(O)R$^8$ where each R$^8$ is independently hydrogen, alkyl, alkenyl, cycloalkyl, cycloalkylalkyl, aralkyl or aryl. The alkenylene chain may be attached to the rest of the molecule through any two carbons within the chain.

"Cycloalkyl" refers to a stable monovalent monocyclic or bicyclic hydrocarbon radical consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents independently selected from the group consisting of alkyl, aryl, aralkyl, halo, haloalkyl, hydroxy, alkoxy, haloalkoxy, cyano, nitro, mercapto, alkylthio, cycloalkyl, —N(R$^8$)$_2$, —C(O)OR$^8$, —C(O)N(Rs)$_2$ or —N(R$^8$)C(O)R$^8$ where each R$^8$ is independently hydrogen, alkyl, alkenyl, cycloalkyl, cycloalkylalkyl, aralkyl or aryl.

"Cycloalkylalkyl" refers to a radical of the formula —R$_a$R$_d$ where R$_a$ is an alkyl radical as defined above and R$_d$ is a cycloalkyl radical as defined above. The alkyl radical and the cycloalkyl radical may be optionally substituted as defined above.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkoxy" refers to a radical of the formula —OR$_c$ where R$_c$ is an haloalkyl radical as defined above, e.g., trifluoromethoxy, difluoromethoxy, trichloromethoxy, 2,2,2-trifluoroethoxy, 1-fluoromethyl-2-fluoroethoxy, 3-bromo-2-fluoropropoxy, 1-bromomethyl-2-bromoethoxy, and the like.

"Heterocyclyl" refers to a stable 3- to 15-membered ring radical which consists of carbon atoms and from one to five heteroatoms selected from the group consisting of nitrogen, oxygen and sulfur. For purposes of this invention, the heterocyclyl radical may be a monocyclic, bicyclic or tricyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be aromatic or partially or fully saturated. The heterocyclyl radical may not be attached to the rest of the molecule at any heteroatom atom. Examples of such heterocyclyl radicals include, but are not limited to, azepinyl, acridinyl, benzimidazolyl, benzthiazolyl, benzothiadiazolyl, benzoxazolyl, benzodioxolyl, benzodioxinyl, benzopyranyl, benzopyranonyl, benzofuranyl, benzofuranonyl, benzothienyl(benzothiophenyl), benzotriazolyl, carbazolyl, cinnolinyl, decahydroisoquinolyl, dioxolanyl, furanyl, furanonyl, isothiazolyl, imidazolyl, imidazolinyl, imidazolidinyl, isothiazolidinyl, indolyl, indazolyl, isoindolyl, indolinyl, isoindolinyl, indolizinyl, isoxazolyl, isoxazolidinyl, morpholinyl, naphthyridinyl, oxadiazolyl, octahydroindolyl, octahydroisoindolyl, 2-oxopiperazinyl, 2-oxopiperidinyl, 2-oxopyrrolidinyl, 2-oxoazepinyl, oxazolyl, oxazolidinyl, oxiranyl, piperidinyl, piperazinyl, 4-piperidonyl, phenazinyl, phenothiazinyl, phenoxazinyl, phthalazinyl, pteridinyl, purinyl, pyrrolyl, pyrrolidinyl, pyrazolyl, pyrazolidinyl, pyridinyl, pyrazinyl, pyrimidinyl, pyridazinyl, quinazolinyl, quinoxalinyl, quinolinyl, quinuclidinyl, isoquinolinyl, thiazolyl, thiazolidinyl, thiadiazolyl, triazolyl, tetrazolyl, tetrahydrofuryl, triazinyl, tetrahydropyranyl, thienyl, thiamorpholinyl, thiamorpholinyl sulfoxide, and thiamorpholinyl sulfone. Unless stated otherwise specifically in the specification, the term "heterocyclyl" is meant to include heterocyclyl radicals as defined above which are optionally substituted by one or more substituents selected from the group consisting of alkyl, halo, nitro, cyano, haloalkyl, haloalkoxy, aryl, heterocyclyl, heterocyclylalkyl, $-OR^8$, $-R^7-OR^8$, $-C(O)OR^8$, $-R^7-C(O)OR^8$, $-C(O)N(R^8)_2$, $-N(R^8)_2$, $-R^7-N(R^8)_2$, and $-N(R^8)C(O)R^8$ wherein each $R^7$ is a straight or branched alkylene or alkenylene chain and each $R^8$ is independently hydrogen, alkyl, alkenyl, cycloalkyl, cycloalkylalkyl, aralkyl or aryl.

"Heterocyclylalkyl" refers to a radical of the formula $-R_aR_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at the nitrogen atom. The heterocyclyl radical may be optionally substituted as defined above.

As used herein, compounds which are "commercially available" may be obtained from standard commercial sources including Acros Organics (Pittsburgh, Pa.), Aldrich Chemical (Milwaukee Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hannover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandier et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"PTPN12" refers to the Human Genome Organization (HUGO) Nomenclature Committee's name for protein tyrosine phosphatase, non-receptor like 12. PTPN12 is also known as PTP-PEST and PTPG1.

"PTPN1" refers to the HUGO Nomenclature Committee's name for protein tyrosine phosphatase, non-receptor like 1. PTPN1 is also known as PTP1B.

"PTPN2" refers to the Human Genome Organization (HUGO) Nomenclature Commitee's name for protein tyrosine phosphatase, non-receptor like 2. PTPN2 is also known as TC-PTP or T-cell-PTP. The sequence of PTPN2 may be accessed at Genbank, M25393, and is described in Cool et al. (1989) Proc. Natl. Acad. Sci. U.S.A. 86 (14), 5257-5261.

"Therapeutically effective amount" refers to that amount of a compound of formula (I) which, when administered to a mammal, preferably a human, is sufficient to effect treatment, as defined below, for cancer and inflammation in the mammal. The amount of a compound of formula (I) which constitutes a "therapeutcally effective amount" will vary depending on the compound, the condition and its severity, and the age of the mammal to be treated, but can be determined routinely by one of ordinary skill in the art having regard to his own knowledge and to this disclosure.

"Treating" or "treatment" as used herein covers the treatment of cancer, inflammation, or diabetes, preferably cancer or inflammation associated with PTPN12 or PTPN2 activity, or diabetes associated with PTPN1 activity, in a mammal, preferably a human, and includes:

(i) preventing the cancer, inflammation, or diabetes from occurring in a mammal, in particular, when such mammal is predisposed to the condition but has not yet been diagnosed as having it;

(ii) inhibiting the cancer, inflammation or diabetes i.e., arresting its development; or (iii) relieving the cancer, inflammation or diabetes, i.e., causing regression of the condition.

"Insulin resistance" includes diabetes, hyperglycemia, and other disorders associated with insulin receptor (IR) signal transduction.

The compounds of formula (I), or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

The nomenclature used herein for the compounds of formula (I) is a modified form of the I.U.P.A.C. nomenclature system wherein the compounds are named herein as derivatives of the thiazolidine moiety.

Methods of Use

This invention is directed to methods of using compounds of formula (I) and formula (Ia), as set forth above in the Summary of the Invention, and pharmaceutical compositions containing compounds of formula (Ia) in treating diseases of cell hyperproliferation and activation, including cancer and, inflammation.

The methods of the invention can be used prophylactically (i.e., to prevent the disorder of interest from occurring) or therapeutically (i.e., to inhibit or relieve the disorder). As used herein, the term "treating" is used to refer to both prevention of disease, and treatment of pre-existing conditions. The prevention of symptoms is accomplished by administration of the compounds and pharmaceutical compositions of the invention prior to development of overt disease, e.g., to prevent the regrowth of tumors, prevent metastatic growth, diminish restenosis associated with cardiovascular surgery, to prevent or reduce cell migration leading to inflammation and associated tissue damage. Alternatively, the compounds and pharmaceutical compositions of the invention may be administered to a subject in need thereof to treat an ongoing disease, by stabilizing or improving the clinical symptoms of the patient.

The subject, or patient, may be from any mammalian species, e.g. primates, particularly humans; rodents, including mice, rats and hamsters; rabbits; equines; bovines; canines; felines; etc. Animal models are of interest for experimental investigations, providing a model for treatment of human disease.

The susceptibility of a particular cell to treatment according to the invention may be determined by in vitro testing. Typically, a culture of the cell is combined with a subject compound at varying concentrations for a period of time sufficient to allow the active agents to induce cell death or inhibit migration, usually between about one hour and one week. For in vitro testing, cultured cells from a biopsy sample may be used.

The dose will vary depending on mode of administration, specific disorder, patient status, etc. Typically a therapeutic dose will be sufficient to substantially decrease the undesirable cell population in the targeted tissue, while maintaining patient viability. Treatment will generally be continued until there is a substantial reduction, e.g. at least about 50%, decrease in the clinical manifestation of disease, and may be continued until there are essentially none of the undesirable cellular activity detected in the relevant tissue.

The compounds of formula (I) and the compounds of formula (Ia) may also find use in the specific inhibition of signaling pathways mediated by protein tyrosine phosphatases, for example, PTPN12, PTPN2, or PTPNL and as a "positive" control in high throughput screening for other modulating compounds.

The compounds of formula (I) and the compounds of formula (Ia) may also find use as affinity reagents for the isolation and/or purification of phosphatases using the biochemical affinity of the enzyme for inhibitors that act on it. The compounds are coupled to a matrix or gel. The coupled support is then used to separate the enzyme, which binds to the compound, from a sample mixture, e.g., a cell lysate, which may be optionally partially purified. The sample mixture is contacted with the compound coupled support under conditions that minimize non-specific binding. Methods known in the art include columns, gels, capillaries, etc. The unbound proteins are washed free of the resin and the bound proteins are then eluted in a suitable buffer.

The compounds of formula (I) and the compounds of formula (Ia) may also be useful as reagents for studying signal transduction or any of the clinical disorders listed throughout this application, and for use as a positive control in high throughput screening.

Disorders and Conditions of Interest

The conditions and disorders of interest to the present invention are cancer and inflammation, in particular, cancer and inflammation associated with PTPN12 and/or PTPN2 activity. There are many disorders associated with PTPN12 and/or PTPN2 activity including dysregulation of cellular division. Accordingly, the compounds and pharmaceutical compositions of the invention may be used to treat a variety of conditions where there is proliferation and/or migration of smooth muscle cells, and/or inflammatory cells into the intimal layer of a vessel, resulting in restricted blood flow through that vessel, i.e. neointimal occlusive lesions. Occlusive vascular conditions of interest include atherosclerosis, graft coronary vascular disease after transplantation, vein graft stenosis, peri-anastomatic prosthetic graft stenosis, restenosis after angioplasty or stent placement, and the like.

Disorders and conditions where there is hyperproliferation and/or tissue remodelling or repair of reproductive tissue, e.g. uterine, testicular and ovarian carcinomas, endometriosis, squamous and glandular epithelial carcinomas of the cervix, etc. are reduced in cell number by administration of the compounds and pharmaceutical compositions of the invention.

Tumors of interest for treatment include carcinomas, e.g. colon, duodenal, prostate, breast, melanoma, ductal, hepatic, pancreatic, renal, endometrial, stomach, invasive oral cancer, transitional and squamous cell urinary carcinoma etc; hematological malignancies, e.g. childhood acute leukaemia, non-Hodgkin's lymphomas, or chronic lymphocytic leukaemia, non-small cell lung carcinoma, adenocarcinoma, and melanoma. Some cancers of particular interest include breast cancers, wherein ductal carcinoma in situ is the most common type of noninvasive breast cancer.

Other disorders and conditions of interest relate to epidermal hyperproliferation, tissue remodelling and repair. For example, the chronic skin inflammation of psoriasis is associated with hyperplastic epidermal keratinocytes.

In one aspect of the invention, compounds and pharmaceutical compositions of the invention may be used to inhibit the activity of PTPN12 and/or PTPN2 for the treatment of inflammatory disorders and autoimmune conditions including, but not limited to, psoriasis, rheumatoid arthritis, multiple sclerosis, scleroderma, systemic lupus erythematosus, Sjögren's syndrome, atopic dermatitis, asthma, and allergy. Target cells susceptible to the treatment include cells involved in instigating autoimmune reactions as well as those suffering or responding from the effects of autoimmune attack or inflammatory events, and include lymphocytes and fibroblasts.

PTPN12 contains a proline rich motif at its C-terminal and can bind to p130$^{cas}$, which is a focal adhesion associated protein containing an SH3 domain. In normal cells, p130$^{cas}$ becomes highly phosphorylated following integrin dependent activation of the fak and src kinases. This phosphorylation appears to allow tyrosine dependent signalling that has as a consequence the reorganization of actin filaments. Because of the importance of integrin signalling in the cell cytoskeleton, motility and transformation, the action of PTPN12 on p130$^{cas}$ may have dramatic consequences in mammalian development as well as in some physiopathological events. The process of cell migration is crucial for the correct development of a mammalian embryo. In an adult organism, cell migration plays an important role in events like invasion of a wounded space by fibroblasts and endothelial cells and translocation of lymphocytes and neutrophiles to an inflammation site. In cancer, tumor cells also have to migrate in order to reach the circulatory system and disperse throughout the organism. Takekawa, M. et al., *FEBS Lett*. (1994), Vol. 339, pp. 222-228 discloses aberrant transcripts of PTPN12 in cancer cells. The effect of PTPN12 levels on fibroblast motility is described in Garton et al. (1999) J. Biol. Chem. 274(6):3811-3818. Davidson et al. (2001) *EMBO. J.* 20(13):3414-26 discusses a connection of PTPN12 with inflammation. The relationship between PTPN12 and podocyte regulation in kidney is described in Reiser, J. et al., Rapid Communication, *Kidney Int*. (2000), Vol. 57, No. 5, pp. 2035-2042.

PTPN12 is involved in signalling pathways for such important cellular activities as responses to extracellular signals and cell cycle checkpoints. Inhibition of PTPN12 provides a means (for example, by blocking the effect of an extracellular signal) of intervening in these signalling pathways, which are associated with a variety of pathological or clinical conditions. PTPN12 is associated with cell adhesion, cell division and cell migration and thus is implicated in cancer and inflammation.

Another PTP of particular interest is PTPN2. PTPN2 is also known as T-cell protein tyrosine phosphatase (TC-PTP) and was first identified by Cool et al., *Proc. Natl. Acad. Sci.*

(1989), Vol. 86, pp. 5257-5261. PTPN2 exists in two forms generated by alternative splicing: a 48 kDa endoplasmic reticular (ER)-associated form called TC48 (PTP-S4); and a 45-kDa nuclear form called TC45 (PTP-S2). PTPN2 plays a significant role in both hematopoiesis and immune function. You-Ten et al., *J. Exp. Med.* (1997), Vol. 186, No. 5, pp. 683-693 found that PTPN2 −/− mice die between 3-5 weeks of age, exhibiting specific defects in bone marrow (BM), B cell lymphopoeisis, and erythropoiesis, as well as impaired T and B cell functions. Bone marrow transplantation experiments demonstrated that hematopoietic failure in the homozygotes was not due to a stem cell defect but rather stromal cell deficiency.

PTPN2 may play a role in cancer progression and metastases. Mitra, S. K. et al., *Exp. Cell Res.* 15 (2001), Vol. 270, No. 1, pp. 32-44 demonstrated inhibition of anchorage-independent cell growth, adhesion, and cyclin D1 gene expression by a dominant negative mutant PTPN2. Expression of mutant PTPN2 in PyF cells resulted in strong inhibition of anchorage-independent growth in soft agar but had no significant effect on growth in liquid culture. Tumor formation in nude mice was also reduced by the presence of mutant PTPN2.

PTPN2 plays a role in apoptosis, making it a useful target for cancer therapy or as a component of a cancer therapeutic cocktail. Zsigmond, E. et al., *FEBS Lett.* (1999), Vol. 453, No. 3, pp. 308-312, found that overexpression of PTPN2 induced nuclear fragmentation typical of apoptosis. In addition, PTPN2 appears to be active in progressing the early G1 phase of the cell cycle through the NF-kappaB pathway (Ibarra-Sanches, M. J. et al., *Oncogene* (2001), Vol. 20, No. 34, pp. 4728-39). Inhibition of PTPN2 is useful in treating conditions associated with PTPN2 activity, such as inflammation, cancer progression and metastases.

PTPN1 activity is associated with insulin resistance, and diabetes, hyperglycemia, and other disorders associated with insulin receptor (IR) signal transduction. Reduction of PTPN1, for example, is sufficient to increase insulin-dependent metabolic signaling and improve insulin sensitivity (Gum, R. J.; Gaede, L. L.; Koterski, S. L. et al., Diabetes (2003) 52(1):21-8). When PTPN1 is overexpressed, it plays a role in insulin resistance (Ahmad, F. et al., (1997) J. Clin. Invest. 100: 449-458, 1997).

Administration of the Compounds and Pharmaceutical Compositions of the Invention Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington's Pharmaceutical Sciences,* 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disorder or condition associated with hyperproliferation and tissue remodelling or repair in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, e.g., inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel™, corn starch and the like; lubricants such as magnesium stearate or Sterotex™; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, e.g., a gelatin capsule, it may contain, in addition to materials of the above type, a liquid carrier such as polyethylene glycol or a fatty oil.

The pharmaceutical composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 1% by weight of the compound of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, e.g., of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units which can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

Whether in solid, liquid or gaseous form, the pharmaceutical composition of the present invention may contain one or more known pharmacological agents used in the treatment of cancer or inflammation in a mammal, particularly, cancer or inflammation associated with hyperproliferation and tissue remodelling or repair.

The pharmaceutical compositions of the invention may be prepared by methodology well known in the pharmaceutical art. For example, a pharmaceutical composition intended to be administered by injection can be prepared by combining a compound of the invention with water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is from about 0.1 mg to about 20 mg/kg of body weight per day of a compound of the invention, or a pharmaceutically acceptable salt thereof; preferably, from about 0.1 mg to about 10 mg/kg of body weight per day; and most preferably, from about 0.1 mg to about 7.5 mg/kg of body weight per day.

PREFERRED EMBODIMENTS OF THE INVENTION

Of the methods of using compounds of formula (I) or formula (1a) to treat cancer, inflammation, or insulin resistance in a mammal as set forth above in the Summary of the Invention, a preferred group of methods is that group wherein the mammal is human. Of this preferred group, a preferred subgroup of methods is that subgroup wherein the cancer is colorectal, or associated with hyperproliferation or tissue remodelling or repair. Of this preferred subgroup, a preferred class of methods is that class wherein the cancer is associated the activity of PTPN12, PTPN1 and/or PTPN2.

Of this preferred group, subgroup and class of methods set forth above, a preferred subclass of methods is that subclass wherein the compound of formula (I) is a compound of formula (I) wherein:

A is —$R^8$—$C(R^2)$—$N(R^5)$—;

$R^1$ and $R^2$ are each independently =O or =S;

$R^3$ and $R^6$ are each independently selected from the group consisting of hydrogen, alkyl, aryl, aralkyl, halo, haloalkyl, haloalkoxy, nitro, cyano, —N=N—O—$R^{11}$—, —$OR^{10}$, —$C(O)OR^{10}$, —$C(O)N(R^{10})_2$, —$N(R^{10})_2$, —$N(R^{10})C(O)R^{10}$, —$N(R^{10})C(O)OR^{11}$, —$S(O)_tR^{10}$ (where t is 0 to 2), —$S(O)_tN(R^{10})_2$ (where t is 0 to 2), and —$S(O)_tNH$—$R^{14}$;

$R^4$ is hydrogen or alkyl;

$R^5$ is hydrogen or alkyl;

$R^8$ is an optionally substituted straight or branched alkylene or alkenylene chain of two carbons;

each $R^{10}$ is hydrogen, alkyl, aralkyl or aryl; and $R^{11}$ is hydrogen, alkyl or aralkyl; and $R^{14}$ is a thiazole.

Of this preferred subclass of methods, a preferred set of methods is that set wherein the compound of formula (I) is a compound of formula (I) wherein:

A is —$R^8$—C($R^2$)—N($R^5$)—;

$R^1$ and $R^2$ are each independently =O or =S;

$R^3$ is hydrogen, alkyl, alkoxy, aryl, aralkyl, halo, haloalkyl, or haloalkoxy;

$R^4$ is hydrogen or alkyl;

$R^5$ is hydrogen or alkyl;

$R^6$ is —C(O)O$R^{10}$, —C(O)N($R^{10}$)$_2$, —S(O)$_t R^{10}$ (where t is 0 to 2), —S(O)$_t$N($R^{10}$)$_2$ (where t is 0 to 2), oe and —S(O)$_t$NH—$R^{14}$;

$R^8$ is an optionally substituted straight or, branched alkylene or alkenylene chain of two carbons; and each $R^{10}$ is hydrogen, alkyl, aralkyl or aryl.

Of this set of methods, a preferred subset of methods is that subset wherein the compound of formula (I) is a compound of formula (I) wherein:

A is —$R^8$—C($R^2$)—N($R^5$)—;

$R^1$ and $R^2$ are both =O;

$R^3$ is alkyl, alkoxy, haloalkyl or haloalkoxy;

$R^4$ is hydrogen;

$R^5$ is hydrogen or alkyl;

$R^6$ is —S(O)$_2$N($R^{10}$)$_2$;

$R^8$ is ethylene;

$R^{10}$ is hydrogen or alkyl; and $R^{14}$ is a thiazole.

Alternatively, of the methods of using compounds of formula (I) to treat cancer, inflammation or insulin resistance as set forth above in the Summary of the Invention, a preferred group of methods is that group wherein the compound of formula (I) is a compound of formula (I) wherein A is an optionally substituted straight or branched alkylene chain of four carbons, or an optionally substituted straight or branched alkenylene chain of four carbons.

Another preferred group of methods is that group wherein the compound of formula (I) is a compound of formula (I) wherein A is —$R^8$—C($R^2$)—N($R^5$)— or —$R^8$—N($R^5$)—C($R^2$)—.

Another preferred group of methods is that group wherein the compound of formula (I) is a compound of formula (I) wherein A is —$R^8$—O—C($R^2$)—, —$R^7$—O—C($R^2$)—$R^7$—, or —$R^9$—C($R^2$)—.

Another preferred group of methods is that group wherein the compound of formula (I) is a compound of formula (I) wherein A is —$R^8$—O—$R^7$—, —$R^8$—S(O)$_t$—$R^7$— (where t is 0 to 2), or —$R^9$—O—.

Another preferred group of methods is that group wherein the compound of formula (I) is a compound of formula (I) wherein A is —$R^7$—C($R^2$)—N($R^5$)—S(O)$_t$— (where t is 0 to 2) or.

Another preferred group of methods is that group wherein the compound of formula (I) is a compound of formula (I) wherein A is —$R^8$—N($R^5$)—$R^7$—.

Another preferred group of methods is that group wherein the compound of formula (I) is a compound of formula (I) wherein A is —$R^8$—C($R^2$)—N($R^5$)—S(O)$_t$NH—$R^{14}$.

Of the methods and the preferred group of methods set forth above, a preferred subgroup of methods is that subgroup wherein the compound of formula (I) is a compound of formula (I) wherein $R^1$ is =O.

Another preferred subgroup of methods is that subgroup wherein the compound of formula (I) is a compound of formula (I) wherein $R^1$ is =S.

Of the methods and the preferred groups and subgroups of methods set forth above, a preferred class of methods is that class wherein the compound of formula (I) is a compound of formula (I) wherein $R^2$ is =O.

Another preferred class of methods is that class wherein the compound of formula (I) is a compound of formula (I) wherein $R^2$ is =S.

Of the methods and the preferred groups, subgroups and classes of methods as set forth above, a preferred subclass of methods is that subclass wherein the compound of formula (I) is a compound of formula (I) wherein $R^3$ is hydrogen, alkyl, alkenyl, cycloalkyl, cycloalkylalkyl, or haloalkyl.

Another preferred subclass of methods is that subclass wherein the compound of formula (I) is a compound of formula (I) wherein $R^3$ is aryl, aralkyl, or aralkenyl.

Another preferred subclass of methods is that subclass wherein the compound of formula (I) is a compound of formula (I) wherein $R^3$ is halo, haloalkoxy, or —O$R^{10}$.

Another preferred subclass of methods is that subclass wherein the compound of formula (I) is a compound of formula (I) wherein $R^3$ is nitro, cyano, or —N=N—O—$R^{11}$.

Another preferred subclass of methods is that subclass wherein the compound of formula (I) is a compound of formula (I) wherein $R^3$ is —C(O)O$R^{10}$ or —C(O)N($R^{10}$)$_2$.

Another preferred subclass of methods is that subclass wherein the compound of formula (I) is a compound of formula (I) wherein $R^3$ is —N($R^{10}$)$_2$, —N($R^{10}$)C(O)$R^{10}$, or —N($R^{10}$)C(O)O$R^{11}$.

Another preferred subclass of methods is that subclass wherein the compound of formula (I) is a compound of formula (I) wherein $R^3$ is —S(O)$_t R^{10}$ (where t is 0 to 2) or —S(O)$_t$N($R^{10}$)$_2$ (where t is 0 to 2).

Another preferred subclass of methods is that subclass wherein the compound of formula (I) is a compound of formula (I) wherein $R^3$ is heterocyclyl or heterocyclylalkyl.

Of the methods and the preferred groups, subgroups, classes and subclasses of methods set forth above, a preferred set of methods is that set wherein the compound of formula (I) is a compound of formula (I) wherein $R^4$ is hydrogen, alkyl, haloalkyl, cycloalkyl, or cycloalkylalkyl.

Another preferred set of methods is that set wherein the compound of formula (I) is a compound of formula (I) wherein $R^4$ is aralkyl or aryl.

Another preferred set of methods is that set wherein the compound of formula (I) is a compound of formula (I) wherein $R^4$ is heterocyclyl or heterocyclylalkyl.

Of the methods and the preferred groups, subgroups, classes, subclasses and sets of methods as set forth above, a preferred subset of methods is that subset wherein the compound of formula (I) is a compound of formula (I) wherein $R^6$ is hydrogen, alkyl, alkenyl, cycloalkyl, cycloalkylalkyl, or haloalkyl.

Another preferred subset of methods is that subset wherein the compound of formula (I) is a compound of formula (I) wherein $R^6$ is aryl, aralkyl, or aralkenyl.

Another preferred subset of methods is that subset wherein the compound of formula (I) is a compound of formula (I) wherein $R^6$ is halo, haloalkoxy, or —O$R^{10}$.

Another preferred subset of methods is that subset wherein the compound of formula (I) is a compound of formula (I) wherein $R^6$ is nitro, cyano, or —N=N—O—$R^{11}$.

Another preferred subset of methods is that subset wherein the compound of formula (I) is a compound of formula (I) wherein $R^6$ is —C(O)O$R^{10}$ or —C(O)N($R^{10}$)$_2$.

Another preferred subset of methods is that subset wherein the compound of formula (I) is a compound of formula (I) wherein $R^6$ is —N($R^{10}$)$_2$, —N($R^{10}$)C(O)$R^{10}$, or —N($R^{10}$)C(O)O$R^{11}$.

Another preferred subset of methods is that subset wherein the compound of formula (I) is a compound of formula (I) wherein $R^6$ is —S(O)$_t$R$^{10}$ (where t is 0 to 2) or —S(O)$_t$N(R$^{10}$)$_2$ (where t is 0 to 2).

Another preferred subset of methods is that subset wherein the compound of formula (I) is a compound of formula (I) wherein $R^6$ is heterocyclyl or heterocyclylalkyl.

Of the methods of using compounds of formula (Ia), a preferred subgroup of methods is that subgroup wherein the cancer is associated with the colon, or colorectal cancer, or cancer associated with hyperproliferation or tissue remodelling or repair. Of this preferred subgroup, a preferred class of methods is that class wherein the cancer is associated the activity of PTPN12 or PTPN2.

Of this preferred group, subgroup and class, a preferred subclass of methods is that subclass wherein the compound of formula (Ia) is a compound of formula (Ia) wherein:

A is —R$^{8a}$—C(R$^{2a}$)—N(R$^{5a}$)—;
$R^{1a}$ and $R^{2a}$ are each independently =O or =S;
$R^{3a}$ is alkyl, aryl, aralkyl, chloro, iodo, bromo, haloalkyl, haloalkoxy, nitro, cyano, —N=N—O—R$^{11a}$, —OR$^{12a}$, —C(O)OR$^{10a}$, —C(O)N(R$^{10a}$)$_2$, —N(R$^{12a}$)$_2$, —N(R$^{10a}$)C(O)R$^{10a}$, —N(R$^{10a}$)C(O)OR$^{11a}$, —S(O)$_t$R$^{10a}$ (where t is 0 to 2), or —S(O)$_t$N(R$^{10a}$)$_2$ (where t is 0 to 2);
$R^{4a}$ is hydrogen or alkyl;
$R^{5a}$ is hydrogen or alkyl;
$R^{6a}$ is alkyl, aryl, aralkyl, halo, haloalkyl, haloalkoxy, nitro, cyano, —N=N—O—R$^{11a}$, —C(O)N(R$^{10a}$)$_2$, —N(R$^{10a}$)$_2$, —N(R$^{10a}$)C(O)R$^{10a}$, —N(R$^{10a}$)C(O)OR$^{11a}$, —S(O)$_t$R$^{10a}$ (where t is 0 to 2), —S(O)$_t$N(R$^{10a}$)$_2$ (where t is 0 to 2), or —S(O)$_t$NH—R$^{14a}$;
each $R^{8a}$ is an optionally substituted straight or branched alkylene or alkenylene chain of two carbons;
each $R^{10a}$ is hydrogen, alkyl, aralkyl or aryl;
$R^{11a}$ is hydrogen, alkyl or aralkyl;
$R^{12a}$ is hydrogen, aryl or aralkyl; and
$R^{14a}$ is a thiazole.

Of this preferred subclass of methods, a preferred set of methods is that set wherein the compound of formula (Ia) is a compound of formula (Ia) wherein:

A is —R$^{8a}$—C(R$^{2a}$)—N(R$^{5a}$)—;
$R^{1a}$ and $R^{2a}$ are each independently =O or =S;
$R^{3a}$ is alkyl, aryl, aralkyl, chloro, iodo, bromo, haloalkyl, or haloalkoxy;
$R^{4a}$ is hydrogen or alkyl;
$R^{5a}$ is hydrogen or alkyl;
$R^{6a}$ is —C(O)N(R$^{10a}$)$_2$, —S(O)$_t$R$^{10a}$ (where t is 0 to 2), —S(O)$_t$N(R$^{10a}$)$_2$ (where t is 0 to 2), or —S(O)$_t$NH—R$^{14a}$; where each $R^{8a}$ is an optionally substituted straight or branched alkylene or alkenylene chain of two carbons; and
each $R^{10a}$ is hydrogen, alkyl, aralkyl or aryl; and
$R^{14a}$ is a thiazole.

Of this preferred set of methods, a preferred subset of methods is that subset wherein the compound of formula (Ia) is a compound of formula (Ia) wherein:

A is —R$^{8a}$—C(R$^{2a}$)—N(R$^{5a}$)—;
$R^{1a}$ and $R^{2a}$ are both =O;
$R^{3a}$ is alkyl, haloalkyl or haloalkoxy;
$R^{4a}$ is hydrogen;
$R^{5a}$ is hydrogen or alkyl;
$R^{6a}$ is —S(O)$_2$N(R$^{10a}$)$_2$;
$R^{8a}$ is ethylene; and
each $R^{10a}$ is hydrogen or alkyl.

Alternatively, of the methods of using compounds of formula (Ia) to treat inflammation in a mammal as set forth above in the Summary of the Invention, a preferred group of methods is that group wherein the compound of formula (Ia) is a compound of formula (Ia) wherein A is an optionally substituted straight or branched alkylene chain of four carbons or an optionally substituted straight or branched alkenylene chain of four carbons.

Another preferred group is that group of methods wherein the compound of formula (Ia) is a compound of formula (Ia) wherein A is —R$^{8a}$—C(R$^{2a}$)—N(R$^{5a}$)— or —R$^{8a}$—N(R$^{5a}$)—C(R$^{2a}$)—.

Another preferred group is that group of methods wherein the compound of formula (Ia) is a compound of formula (Ia) wherein A is —R$^{8a}$—O—C(R$^{2a}$)—, —R$^{7a}$—O—C(R$^{2a}$)—R$^{7a}$—, or —R$^{9a}$—C(R$^{2a}$)—.

Another preferred group is that group of methods wherein the compound of formula (Ia) is a compound of formula (Ia) wherein A is —R$^{8a}$—O—R$^{7a}$—, —R$^{8a}$—S(O)$_t$—R$^{7a}$— (where t is 0 to 2), or —R$^{9a}$—O—.

Another preferred group is that group of methods wherein the compound of formula (Ia) is a compound of formula (Ia) wherein A is —R$^{7a}$—C(R$^{2a}$)—N(R$^{5a}$)—S(O)$_t$— (where t is 0 to 2).

Another preferred group is that group of methods wherein the compound of formula (Ia) is a compound of formula (Ia) wherein A is —R$^{8a}$—N(R$^{5a}$)—R$^{7a}$— or —R$^{9a}$—N(R$^{5a}$)—.

Of the methods and the preferred groups of methods set forth above, a preferred subgroup of methods is that subgroup wherein the compound of formula (Ia) is a compound of formula (Ia) wherein $R^{1a}$ is =O.

Another preferred subgroup is that subgroup of methods wherein the compound of formula (Ia) is a compound of formula (Ia) wherein $R^{1a}$ is =S.

Of the methods and preferred groups and subgroups of methods set forth above, a preferred class of methods is that class wherein the compound of formula (Ia) is a compound of formula (Ia) wherein $R^{2a}$ is =O.

Another preferred class is that class of methods wherein the compound of formula (Ia) is a compound of formula (Ia) wherein $R^{2a}$ is =S.

Of the methods and the preferred groups, subgroups and classes of methods set forth above, a preferred subclass of methods is that subclass wherein the compound of formula (Ia) is a compound of formula (Ia) wherein $R^{3a}$ is alkyl, alkenyl, cycloalkyl, cycloalkylalkyl or haloalkyl.

Another preferred subclass is that subclass of methods wherein the compound of formula (Ia) is a compound of formula (Ia) wherein $R^{3a}$ is chloro, iodo, bromo, haloalkoxy or —OR$^{10a}$.

Another preferred subclass is that subclass of methods wherein the compound of formula (Ia) is a compound of formula (Ia) wherein $R^{3a}$ is nitro, cyano, or —N=N—O—R$^{11a}$.

Another preferred subclass is that subclass of methods wherein the compound of formula (Ia) is a compound of formula (Ia) wherein $R^{3a}$ is —C(O)OR$^{10a}$ or —C(O)N(R$^{10a}$)$_2$.

Another preferred subclass is that subclass of methods wherein the compound of formula (Ia) is a compound of formula (Ia) wherein $R^{3a}$ is —N(R$^{12a}$)$_2$, —N(R$^{10a}$)C(O)R$^{10a}$ or —N(R$^{10a}$)C(O)OR$^{11a}$.

Another preferred subclass is that subclass of methods wherein the compound of formula (Ia) is a compound of formula (Ia) wherein $R^{3a}$ is —S(O)$_t$R$^{10}$ (where t is 0 to 2) or —S(O)$_t$N(R$^{10a}$)$_2$ (where t is 0 to 2).

Another preferred subclass is that subclass of methods wherein the compound of formula (Ia) is a compound of formula (Ia) wherein $R^{3a}$ heterocyclylalkyl.

Of the methods and the preferred groups, subgroups, classes and subclasses of methods set forth above, a preferred set is that set of methods wherein the compound of formula (Ia) is a compound of formula (Ia) wherein $R^{4a}$ is hydrogen, alkyl, haloalkyl, cycloakyl, or cycloalkyl.

Another preferred set is that set of methods wherein the compound of formula (Ia) is a compound of formula (Ia) wherein $R^{4a}$ is aralkyl or aryl.

Another preferred set is that set of methods wherein the compound of formula (Ia) is a compound of formula (Ia) wherein $R^{4a}$ is heterocyclyl or heterocyclylalkyl.

Of the methods and the groups, subgroups, classes, subclasses and sets of methods set forth above, a preferred subset is that subset of methods wherein the compound of formula (Ia) is a compound of formula (Ia) wherein $R^{6a}$ is alkyl, alkenyl, cycloalkyl, cycloalkylalkyl or haloalkyl.

Another preferred subset is that subset of methods wherein the compound of formula (Ia) is a compound of formula (Ia) wherein $R^{6a}$ is halo or haloalkoxy.

Another preferred subset is that subset of methods wherein the compound of formula (Ia) is a compound of formula (Ia) wherein $R^{6a}$ is nitro, cyano, or —N=N—O—$R^{11a}$.

Another preferred subset is that subset of methods wherein the compound of formula (Ia) is a compound of formula (Ia) wherein $R^{6a}$ is —C(O)N($R^{10a}$)$_2$.

Another preferred subset is that subset of methods wherein the compound of formula (Ia) is a compound of formula (Ia) wherein $R^{6a}$ is —N($R^{10a}$)$_2$, —N($R^{10a}$)C(O)$R^{10a}$ or —N($R^{10a}$)C(O)O$R^{11a}$.

Another preferred subset is that subset of methods wherein the compound of formula (Ia) is a compound of formula (Ia) wherein $R^{6a}$ is —S(O)$_t R^{10}$ (where t is 0 to 2) or —S(O)$_t$N($R^{10a}$)$_2$ (where t is 0 to 2).

Another preferred subset is that subset of methods wherein the compound of formula (Ia) is a compound of formula (Ia) wherein $R^{6a}$ heterocyclylalkyl or heterocyclylalkyl.

Of the pharmaceutical compositions comprising a pharmaceutically acceptable excipient and a compound of formula (Ia) as set forth above in the Summary of the Invention, a preferred group of pharmaceutical compositions is that group wherein the compound of formula (Ia) is a compound of formula (Ia) wherein A is an optionally substituted straight or branched alkylene chain of four carbons or an optionally substituted straight or branched alkenylene chain of four carbons.

Another preferred group is that group of pharmaceutical compositions wherein the compound of formula (Ia) is a compound of formula (Ia) wherein A is —$R^{8a}$—C($R^{2a}$)—N($R^{5a}$)— or —$R^{8a}$—N($R^{5a}$)—C($R^{2a}$)—.

Another preferred group is that group of pharmaceutical compositions wherein the compound of formula (Ia) is a compound of formula (Ia) wherein A is —$R^{8a}$—O—C($R^{2a}$)—, —$R^{7a}$—O—C($R^{2a}$)—$R^{7a}$—, or —$R^{9a}$—C($R^{2a}$)—.

Another preferred group is that group of pharmaceutical compositions wherein the compound of formula (Ia) is a compound of formula (Ia) wherein A is —$R^{8a}$—O—$R^{7a}$—, —$R^{8a}$—S(O)$_t$—$R^{7a}$— (where t is 0 to 2), or —$R^{9a}$—O—.

Another preferred group is that group of pharmaceutical compositions wherein the compound of formula (Ia) is a compound of formula (Ia) wherein A is —$R^{7a}$—C($R^{2a}$)—N($R^{5a}$)—S(O)$_t$— (where t is 0 to 2).

Another preferred group is that group of pharmaceutical compositions wherein the compound of formula (Ia) is a compound of formula (Ia) wherein A is —$R^{8a}$—N($R^{5a}$)—$R^{7a}$— or —$R^{9a}$—N($R^{5a}$)—.

Of the pharmaceutical compositions and the preferred groups of pharmaceutical compositions set forth above, a preferred subgroup of pharmaceutical compositions is that subgroup wherein the compound of formula (Ia) is a compound of formula (Ia) wherein $R^{1a}$ is =O.

Another preferred subgroup is that subgroup of pharmaceutical compositions wherein the compound of formula (Ia) is a compound of formula (Ia) wherein $R^{1a}$ is =S.

Of the pharmaceutical compositions and the preferred groups and subgroups of pharmaceutical compositions set forth above, a preferred class of pharmaceutical compositions is that class wherein the compound of formula (Ia) is a compound of formula (Ia) wherein $R^{2a}$ is =O.

Another preferred class is that class of pharmaceutical compositions wherein the compound of formula (Ia) is a compound of formula (Ia) wherein $R^{2a}$ is =S.

Of the pharmaceutical compositions and the preferred groups, subgroups and classes of pharmaceutical compositions set forth above, a preferred subclass of pharmaceutical compositions is that subclass wherein the compound of formula (Ia) is a compound of formula (Ia) wherein $R^{3a}$ is alkyl, alkenyl, cycloalkyl, cycloalkylalkyl or haloalkyl.

Another preferred subclass is that subclass of pharmaceutical compositions wherein the compound of formula (Ia) is a compound of formula (Ia) wherein $R^{3a}$ is chloro, iodo, bromo, haloalkoxy or —O$R^{10a}$.

Another preferred subclass is that subclass of pharmaceutical compositions wherein the compound of formula (Ia) is a compound of formula (Ia) wherein $R^{3a}$ is nitro, cyano, or —N=N—O—$R^{11a}$.

Another preferred subclass is that subclass of pharmaceutical compositions wherein the compound of formula (Ia) is a compound of formula (Ia) wherein $R^{3a}$ is —C(O)O$R^{10a}$ or —C(O)N($R^{10a}$)$_2$.

Another preferred subclass is that subclass of pharmaceutical compositions wherein the compound of formula (Ia) is a compound of formula (Ia) wherein $R^{3a}$ is —N($R^{12a}$)$_2$, —N($R^{10a}$)C(O)$R^{10a}$ or —N($R^{10a}$)C(O)O$R^{11a}$.

Another preferred subclass is that subclass of pharmaceutical compositions wherein the compound of formula (Ia) is a compound of formula (Ia) wherein $R^{3a}$ is —S(O)$_t R^{10}$ (where t is 0 to 2) or —S(O)$_t$N($R^{10a}$)$_2$ (where t is 0 to 2).

Another preferred subclass is that subclass of pharmaceutical compositions wherein the compound of formula (Ia) is a compound of formula (Ia) wherein $R^{3a}$ heterocyclylalkyl.

Of the pharmaceutical compositions and the preferred groups, subgroups, classes and subclasses of pharmaceutical compositions set forth above, a preferred set is that set of pharmaceutical compositions wherein the compound of formula (Ia) is a compound of formula (Ia) wherein $R^{4a}$ is hydrogen, alkyl, haloalkyl, cycloakyl, or cycloalkyl.

Another preferred set is that set of pharmaceutical compositions wherein the compound of formula (Ia) is a compound of formula (Ia) wherein $R^{4a}$ is aralkyl or aryl.

Another preferred set is that set of pharmaceutical compositions wherein the compound of formula (Ia) is a compound of formula (Ia) wherein $R^{4a}$ is heterocyclyl or heterocyclylalkyl.

Of the pharmaceutical compositions and the groups, subgroups, classes, subclasses and sets of pharmaceutical compositions set forth above, a preferred subset is that subset of pharmaceutical compositions wherein the compound of formula (Ia) is a compound of formula (Ia) wherein $R^{6a}$ is alkyl, alkenyl, cycloalkyl, cycloalkylalkyl or haloalkyl.

Another preferred subset is that subset of pharmaceutical compositions wherein the compound of formula (Ia) is a compound of formula (Ia) wherein $R^{6a}$ is halo or haloalkoxy.

Another preferred subset is that subset of pharmaceutical compositions wherein the compound of formula (Ia) is a compound of formula (Ia) wherein $R^{6a}$ is nitro, cyano, or —N=N—O—$R^{11a}$.

Another preferred subset is that subset of pharmaceutical compositions wherein the compound of formula (Ia) is a compound of formula (Ia) wherein $R^{6a}$ is —C(O)N($R^{10a}$)$_2$.

Another preferred subset is that subset of pharmaceutical compositions wherein the compound of formula (Ia) is a compound of formula (Ia) wherein $R^{6a}$ is —N($R^{10a}$)$_2$, —N($R^{10a}$)C(O)$R^{10a}$ or —N($R^{10a}$)C(O)O$R^{11a}$.

Another preferred subset is that subset of pharmaceutical compositions wherein the compound of formula (Ia) is a compound of formula (Ia) wherein $R^{6a}$ is —S(O)$_t R^{10}$ (where t is 0 to 2) or —S(O)$_t$N($R^{10a}$)$_2$ (where t is 0 to 2).

Another preferred subset is that subset of pharmaceutical compositions wherein the compound of formula (Ia) is a compound of formula (Ia) wherein $R^{6a}$ is heterocyclyl or heterocyclylalkyl.

Of the methods of treating a mammalian cell with a compound of formula (I) wherein the method comprises administering the compound of formula (I) to a mammalian cell and the compound of formula (I) is capable of inhibiting the activity of PTPN12, PTPN2 and/or PTPN1, a preferred group of methods is that group wherein the mammalian cell is treated in vitro.

Another preferred group of these methods is that group wherein the mammalian cell is treated in vivo.

Another preferred group of these methods is that group wherein the inhibition of activity results in a reduction of cell adhesion, cell division, cell migration, or tumor growth.

Another preferred group of these methods is that group wherein the inhibition of activity results in control of lymphocyte activation.

Another preferred group of these methods is that group wherein the inhibition of PTPN1 activity results in control of insulin resistance.

Preparation of the Compounds of Formula (I) and Formula (Ia)

Compounds of formula (I) and formula (Ia) in the methods and pharmaceutical compositions of the invention may be prepared according to methods known to one skilled in the art, or by the methods similar to those disclosed in Gorishnii, V. Ya. et al., *Farm. Zh. (Kiev)* (2001), Vol. 2, pp. 64-67; Gorishnyi, V. Ya. et al., *Farm. Zh. (Kiev)* (1995), Vol. 4, pp. 50-53; PCT Published Patent Application WO 00/76988; European Patent Specification 0 047109; U.S. Pat. No. 5,310,618; or U.S. Pat. No. 4,965,155; or by the following method.

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein.

The use of protecting groups is described in detail in Green, T. W. and P. G. M. Wutz, *Protective Groups in Organic Synthesis* (1991), 2nd Ed., Wiley-Interscience. The protecting group may also be a polymer resin such as a Wang resin or a 2-chlorotrityl chloride resin.

It will also be appreciated by those skilled in the art, although such protected derivatives of compounds of formulae (I), as described above in the Summary of the Invention, may not possess pharmacological activity as such, they may be administered to a mammal with cancer or inflammation and thereafter metabolized in the body to form compounds of the invention which are pharmacologically active. Such derivatives may therefore be described as "prodrugs". All prodrugs of compounds of formula (I) and formula (Ia) are included within the scope of the invention.

The following Reaction Scheme depicts the preparation of compounds of formula (I) where p, A, $R^1$, $R^3$, $R^4$ and $R^6$ are described above in the Summary of the Invention, and X is halo and $R^{13}$ is hydrogen:

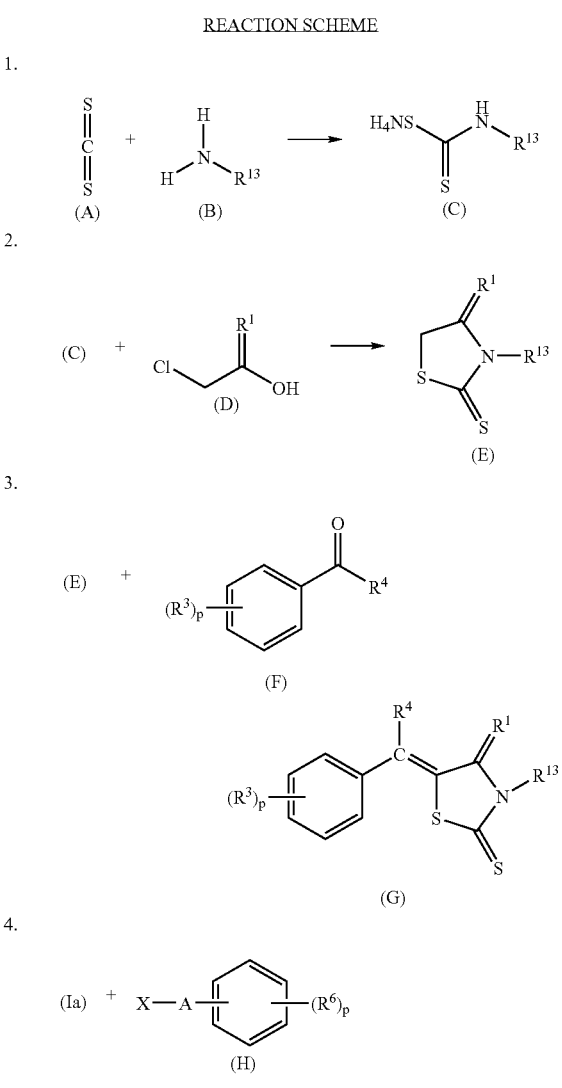

-continued

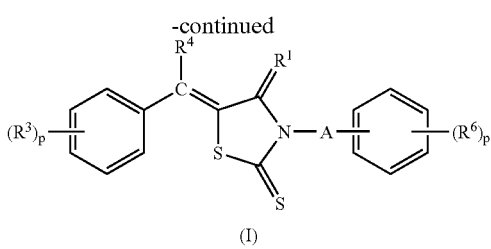

(I)

In this general scheme, starting components may be obtained from sources such as Aldrich, or synthesized according to sources known to those of ordinary skill in the art, e.g., Smith and March, *March's Advanced Organic Chemistry: Reactions, Mechanisms, and Structure,* 5th edition (Wiley Interscience, New York).

In general, dithiocarbamate compounds of formula (C) may be prepared according to Step 1 of the reaction scheme depicted herein, whereby carbon disulfide (i.e., the compound of formula (A)) at a concentration of about 3.5 moles/liter is reacted with about an equimolar quantity of an amine compound of formula (B), in the presence of ammonium hydroxide solution at about 0° C. The admixture is warmed to ambient temperature, stirred for up to about 18 hours, and concentrated to dryness. The resulting substance is a compound of formula (C).

Rhodanine-derived compounds of formula (E) can be prepared under cyclization conditions according to schemes known to those of ordinary skill in the art. For instance, a compound of formula (E) is formed according to Step 2 of the reaction scheme depicted herein, whereby the foregoing quantity of the compound of formula (C) is reacted with about an equimolar quantity of a compound of formula (D) (wherein $R^1$ is O or S) or a basic salt thereof, in an aqueous solution (at about 0° C.) alkalized with dilute sodium carbonate. The reaction mixture is warmed to ambient temperature, admixed with about 6.4 volumes of warm 5 M hydrochloric acid (about 70° C.), and heated to about 90° C. for about 1 hour. After cooling, the resulting precipitate is isolated by filtration, washed with water and allowed to dry, affording a compound of formula (E).

Compounds of formula (F) can be obtained from sources such as Aldrich, or prepared according to schemes known to those of ordinary skill in the art. In one aspect, nitro-substituted benzaldehyde compounds may be prepared under standard aromatic substitution conditions, such as by treatment of benzaldehyde with nitric acid and sulfuric acid. In another aspect, halogen-substituted benzaldehyde compounds may be prepared under standard aromatic substitution conditions, such as by treatment of benzaldehyde with naturally-occurring diatomic halogen compounds (i.e., $F_2$, $Cl_2$, $Br_2$, or $I_2$) with iron metal. In yet another aspect, alkyl-substituted benzaldehyde compounds may be prepared under standard aromatic substitution conditions, such as by Friedel-Crafts alkylation of benzaldehyde with an alkyl halide in the presence of an aluminum halide compound. Such treatments normally produce mixtures comprising compounds with substitutions in various different ring positions, though specific chemical properties of the reagents used, particularly the aromatic compound, may promote the synthesis of certain compounds with specific substitutions at desired ring positions as major synthesis products. Collection of pure major and/or minor synthesis products may be achieved with the use of a preparative separation and isolation technique such as high performance liquid chromatography (HPLC).

Compounds of formula (G) can be prepared under standard condensation reaction conditions according to schemes known to those of ordinary skill in the art. For instance, a compound of formula (G) is formed according to Step 3 of the reaction scheme depicted herein, whereby a compound of formula (E) is combined with about an equimolar quantity of a substituted benzene compound of formula (F) (wherein $R^3$ and $R^4$ are selected from constituents as defined in the Summary of the Invention) in an aqueous solution containing sodium acetate and acetic acid. The reaction is heated to reflux for up to 16 hours with stirring. After cooling, the resulting precipitate is isolated by filtration, washed with water and allowed to dry, affording a compound of formula (G), as a stereoisomer, stereoisomer mixture or as a pharmaceutically acceptable salt thereof.

Compounds of formula (G) wherein $R^{11}$ is hydrogen is reacted with a compound of formula (H) under standard amine alkylation conditions (as depicted in Step 4 above) to afford a compound of formula (I). In a separate optional aspect, a compound of formula (C) wherein $R^{11}$ is hydrogen may be reacted with a compound of formula (H) under standard amine alkylation conditions, the product of which can then proceed sequentially through Steps 2 and 3 of the reaction scheme as depicted herein, to afford a compound of formula (I). In another separate optional aspect, a compound of formula (E) wherein $R^{11}$ is hydrogen may be reacted with a compound of formula (H) under standard amine alkylation conditions, the product of which can then proceed through Step 3 of the reaction scheme as depicted herein, to afford a compound of formula (I).

Compounds of formula (Ia) as defined above in the Summary of the Invention may be prepared in a similar manner as described above.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLE 1

Enzyme Preparation and Use

A. PTPN2

PTPN2 was cloned from a human placental cDNA library in the IMPACT™ (New England BioLabs) bacterial expression system. The technology was first described by Chong et al., *Gene* (1997), Vol. 192, pp. 271-281. The IMPACT™ Protein Purification System was purchased commercially from New England BioLabs. The resulting product was used in the development of a protein phosphatase assay for high-throughput screening (HTS) of target molecules and in other assays described herein (see Example 2).

Biochemical analysis performed on recombinant human PTPN2 fusion protein exhibited protein phosphatase activity in the order of 1500 to 2500 pmol/min/μg measured as phosphate release from a synthetic tyrosine phosphorylated peptide. This activity was considered to be in the high range as compared to other recombinant protein tyrosine phosphatases assayed. PTPN2 preparations were subsequently used extensively in in vitro assays for the initial discovery of compounds having the ability to inhibit PTPN2 activity.

B. PTPN12

PTPN12 was cloned in the IMPACT™ (New England BioLabs) bacterial expression system. The IMPACT™ Protein Purification System was purchased commercially from New England BioLabs.

1. Cloning of Truncated Human PTPN12 into pTWIN-II Expression Vector

Expression of human truncated PTPN12 (PTP-PEST-N) as a fusion protein required that the cDNA be ligated into the polyclonal site situated in frame and upstream of the intein gene of the IMPACT™ expression vector pTWIN-II. The truncated version was used as it was far easier to handle and gave parallel results to the full length protein in comparison testing. For the purpose of simplicity, PTP-PEST-N will be used interchangeably with PTPN12 in these Examples.

The PTPN12 coding sequence was generated by polymerase chain reaction (PCR) using gene-specific primers.

2. Human PTPN12 Expression and Purification

Active PTPN12 enzyme is expressed from the IMPACT™ vector system in the bacterial strain ER2566. Recombinant PTPN12 protein is purified from bacterial cells using affinity chromatography on chitin-agarose beads followed by a chemical process whereby PTPN12 is released from its affinity tag. A complete quantitative and qualitative analysis of the protein is monitored using Coomassie-Blue staining of SDS-PAGE separated preparations and by PTPN12-specific western blotting. PTPN12 is produced at levels in the range of 0.1-0.5 mg per liter of bacterial cell culture.

3. PTPN12 In vitro Phosphatase Assay

Biochemical analysis is performed on recombinant human PTPN12 fusion protein. Typically, the PTPN12 preparations are found to exhibit protein phosphatase reactivity in the order of 1500 to 2500 pmol/min/μg measured as phosphate release from a synthetic tyrosine phosphorylated peptide. This activity is considered to be in the high range as compared to other recombinant protein tyrosine phosphatases. PTPN12 preparations were subsequently used extensively in in vitro assays for the initial discovery of compounds having the ability to inhibit PTPN12 activity.

EXAMPLE 2

In Vitro Activity Profile for Phosphatases

Compounds of formula (I) and formula (Ia) were tested in the following assay for their ability to inhibit the activity of the desired phosphatase.

A. Reagent Preparation

1. Malachite Green-Ammonium Molybdate Reagent

Two solutions were first prepared. Solution 1 contained 4.2% ammonium molybdate tetrahydrate (Sigma, Cat# A-7302) in 4 N HCl. Solution 2 contained 0.045% Malachite Green (Sigma, Cat. # M-9636). The two solutions were mixed as follows: 250 mL of solution 1 and 750 mL solution 2 with constant stirring for 20 min. The resulting mixture was filtered through 0.22 μM filter (one can use Nalgene™ bottle top vacuum filters Cat # 28199-317). The solution was stored in a brown bottle at 4° C.

B. Preparation of 1 mM ppC SRC 60 Substrate

The peptide sequence: TSTEPQY(P0$_4$) QPGENL (SEQ ID NO: 2 was prepared by conventional methods. Of this, 154 mg was dissolved in 100 mLdH$_2$0 and the solution vortexed until the peptide dissolved completely. The ppC SRC 60 was then stored in 1 mL aliquots at −20 C. This is the "Substrate" used for preparing the substrate working stock solution.

C. Procedure for Assay

The enzyme (phosphatase) activity was determined in a reaction that measured phosphate relase from tyrosine phospho-specific peptides using a method first described by Harder et al., Biochem. J. (1994), Vol. 298, pp. 395-401. This is a non-radioactive method for measuring free phosphate by the malachite green method first described by Van Veldhoven and Mannaerts, Anal Biochem. (1987), Vol. 161, pp. 45-48. 10× assay buffer (250 mM Tris:100 mM, β-mercaptoethanol, 50 mM EDTA; pH 7.2) was diluted to 5× concentration (conc.) with distilled H$_2$O (dH$_2$O). Then 71.4 μM of substrate working stock solution was prepared in dH$_2$O.

In a microcentrifuge tube, the required volume. of enzyme stock was pipetted, diluted with the required volume of 5× assay buffer and mixed.

The colour reagent was prepared by thoroughly mixing 10 mL malachite green-ammonium molybdate reagent and 100 μL of 1% Tween-20 (1 mL Tween-20 (BDH, #06435) dissolved in 99 mL dH$_2$O) into a reagent reservoir and stored at room temperature. Approximately 10 mL of colour reagent is required per assay plate, or 100 μL per well.

Sample Compound Preparation

In a Falcon 96 well plate the sample compound was diluted in 1% DMSO (1 mL DMSO (Sigma, Cat. # D-8779) dissolved in 99 mL dH$_2$O and stored at room temperature) such that the concentration of the sample compound working stock solution is ten times the final desired concentration of the compound in the assay.

The working stock solution was prepared as per the required concentration of sample compound in the assay.

The negative control consisted of 5 μl 1% DMSO and 35 μL substrate working stock solution and 10 μL diluted enzyme, per well, and was placed in the first column of wells on the plate. The last column of wells on the plate was reserved for an enzyme blank, which consisted of 5 μL 1% DMSO, 35 μL substrate working stock solution, and 10 μL 5× assay buffer, per well. Test samples were placed in columns 2-11 and consisted of 5 μL sample in 1% DMSO, 35 μL substrate working stock solution, and 10 μL of diluted enzyme, per well, at the desired concentration. Using the repeater function of a Biohit Multichannel™ pipettor, 5 μL of 100 μM sample from the Falcon™ plate columns was added to corresponding Costar™ assay plate columns.

Then 5 μL 1% DMSO was added to column 1 & 12, and 10 μL of 5× assay buffer to column 12.

Using a multichannel pipettor 35 μL of 71.4 μM ppC-SRC 60 substrate was added to all assay wells, then 10 μL of appropriately diluted enzyme was added to the wells on a column by column basis, pausing 5 seconds between columns. Timing started at the first addition.

The assay plate was incubated at room temperature (21° C.) for 15 minutes. The reaction was "stopped" by adding 100 μL color reagent on a column by column basis, pausing 5 seconds between columns. Color was allowed to develop for at least 15 minutes, but no longer than two hours, at room temperature. The plate was "read" on Bio-tek Instruments EL312e microplate Bio-Kinetics™ Reader at 590 nm and the data collected as per instrument manual.

Data analysis was performed as follows. The blank and negative controls were read, and blanks were subtracted from the average of negative control values and sample values, and the % inhibition was expressed by the following formula:

% Inhibition=100−[corrected sample reading/corrected Negative Control reading*100].

Compounds of the invention showed the following profile of inhibition:

TABLE 1

| Compound | Inhibition of PTPN12 IC$_{50}$ | Inhibition of PTPN2 IC$_{50}$ | Inhibition of PTPN1 IC$_{50}$ |
|---|---|---|---|
| 3-[5-(4-methylbenzylidene)-4-oxo-2-thioxothiazolidin-3-yl]-N-(4-sulfamoylphenyl)-propionamide | 1.5 µm | 1.6 | 3.0 µm |
| 3-[5-(4-methylbenzylidene)-4-oxo-2-thioxothiazolidin-3-yl]-N-[4-(thiazol-2-ylsulfamoyl)-phenyl]-propionamide | 1.1 µm | 0.95 µm | 1.5 µm |

EXAMPLE 3

Cell Migration in a Boyden Chamber

A range of cell lines are used in this assay, particularly the prostate cancer cell line PC3 and PTPN12 mouse embryonic fibroblasts (MEFs). The role of PTPN12 in migration was established based on the observations of PTPN12 negative MEFs. Cell adhesion and migration are dynamic biological activities involving the assembly and disassembly of a large number of extracellular and intracellular molecules, for example, actin, which are regulated in turn by protein phosphorylation. Hence locking the system in a phosphorylated (inhibition of phosphatases) or dephosphorylated (inhibition of kinases) state has a profound effect on the assembly/disassembly process and ultimately migration. Migration is reduced in PTPN12 knock-out MEFs. By extension, a PTPN12 inhibitor should reduce cell migration in a Boyden chamber. Therefore, as a readout for PTPN12 activity, the following assay is designed to analyze cell migration in Boyden chambers. The Boyden assay is an experiment used to determine the capacity of a cell type to migrate on extracellular matrix. Unless otherwise indicated, all procedures are performed under sterile conditions in a flow laminar hood and all incubations at 37° C. are performed in the $CO_2$ incubator.

A. Reagents

1. Staining Solution

Calcein AM (Molecular Probes, Cat# C-1430) stain is prepared at 0.5 ug/ml in Hanks Buffered Saline solution (GIBCO/BRL, Cat#14170-112).

2. Fibronectin Solution

A stock solution of fibronectin is prepared by dissolving 5 mg of fibronectin: (Sigma, Cat: F-2006) in 5 mL of sterile phosphate-buffered solution (PBS) by up and down agitation with a P1000™ pipette. The working solution is prepared by mixing 100 µl of this stock solution with 10 mL of sterile PBS.

B. Assay (Tumour Cell Lines)

For tumour cell lines, stock cells (ie. PC3 cells) are grown to 50-70% confluency in T175 flasks. Cells are trypsinized and a suspension prepared to a concentration of 2×10$^5$/ml in media without serum. To the top chamber of each well of the HTS FluoroBlok™ 24-well insert system plates (Cat# 351158) 450 µl of cell suspension (or media for controls) is added. Compounds for testing are prepared as 10× stocks in serum-free media from DMSO stocks, with a maximum final DMSO concentration of 0.25%. 50 µl of compound (or DMSO control) is then added to each top chamber, while 750 µl of media containing 10% fetal bovine serum is added to the bottom chamber as the chemoattractant. The plates are incubated for 20-24 hours at 37° C., 5% $CO_2$. Following incubation, the insert plate is transferred into a second 24-well companion plate containing 0.5 ml of 5 ug/ml calcein AM in HBSS and incubated for 1 hour at 37° C., 5% $CO_2$. Fluorescence of migrated cells is read in a Fluoroskan Ascent FL™ (or equivalent) with bottom reading at excitation/emission wavelength of 485/538 nm. Only those cells that have migrated through the pores of the FluoroBlok™ membrane will be read. For MEFs, the plates are coated on both sides of the membrane with 10 mg/mL fibronectin solution for 18 hours at 4° C. After incubation, the coating solution is removed by aspiration and the excess is washed twice with PBS. Cell seeding and detection are then performed as described for tumour cell lines.

C. Data Analysis

Data is expressed as fluorescence unit (FU) from the sum of middle 25 areas per 24-well or as percentage of migration inhibition by following formula: % of invasion inhibition=100−FU of compound treated cell invasion/FU of DMSO treated cell invasion times 100. Background is subtracted from all values, with background being represented by the media only controls.

TABLE 2

| Compound | % Inhibition of Migration at 25 µM |
|---|---|
| 3-[5-(4-methylbenzylidene)-4-oxo-2-thioxothiazolidin-3-yl]-N-(4-sulfamoylphenyl)-propionamide | 55 |
| 3-[5-(4-methylbenzylidene)-4-oxo-2-thioxothiazolidin-3-yl]-N-[4-(thiazol-2-ylsulfamoyl)-phenyl]-propionamide | 87 |

EXAMPLE 4

The Status of P130$^{CAS}$ Phosphorylation on Western Blots

Phosphotyrosine profiling of PTPN12-heterozygote and PTPN12-knockout mouse fibroblasts showed that a protein migrating at 130 kDa is constitutively hyperphosphorylated in the knockout cells (Côté, J. F., et al., *Biochemistry* (1998), Vol. 37, No. 38, pp. 13128-13137). This protein was identified as being p130$^{cas}$, a protein found in focal adhesion complexes. It also appeared that the hyperphosphorylation of p130$^{cas}$ in the PTPN12 knockout cells resulted in defective cell motility and focal adhesion turnover (Angers-Loustau et al., 1999).

This following assay measures p130$^{cas}$ phosphorylation status as a readout of PTPN12 or other PTP activity such as PTP-1B. Briefly, the general tyrosine phosphorylation state of all cellular proteins is reduced by incubating the cells in suspension and then plating the cells onto fibronectin-coated plates, thereby stimulating tyrosine phosphorylation through the integrin pathway. Following cell lysis, p130$^{cas}$ immunoprecipitation and Western blotting using 4G10 antiphosphotyrosine antibody are used to measure the tyrosine phosphorylation status of p130$^{cas}$. A low level of p130$^{cas}$ tyrosine phosphorylation is indicative of a high PTPN12 activity. The assay is performed using PTPN12 knockout and heterozygote mouse fibroblasts.

A. Materials

1. PTPN12+/− mouse fibroblasts (AC4+/−) and PTPN12−/− mouse fibroblasts (AC6−/−) as kindly provided by Michel Tremblay and colleagues from the Cancer Centre at McGill University.

2. RIPA Buffer is made by mixing 50 mM Tris-HCl pH 7.2, 150 mM NaCl, 0.1% SDS (BioShop, Cat#: SDS 001), 0.5% sodium deoxycholate 10% solution (Sigma, Cat: D-6750), 1% NP40 (BDH Laboratory Supplies, Cat: 56009 2L), 1 mM sodium vanadate (Fisher Scientific, Cat: S454-50) 200 mM solution, and "complete protease inhibitor mixture" (Roche Cat. 1836153).

3. SDS sample buffer is prepared by mixing 62.5 mM Tris-HCl pH 6.8, 20% glycerol (BioShop, Cat#: Gly 001), 2% SDS, 5% β-mercaptoethanol (Acros Organics, Cat#: 12547-2500), and 0.025% bromophenol blue (EM Science, OmniPur™).

B. Fibronectin Stimulation

6-Well plates (Fisher Scientific, Cat: 08-772-1 B, Falcon No. 3530) are coated for 18 hours at 4° C. with a 10 mg/mL fibronectin solution (Sigma, Cat: F-2006, Lot: 109H7602) (density of 1 g/cm$^2$). A volume of 950 µl of the fibronectin solution is added to each well. The plates are washed 2 times by adding 2 mL of PBS at ambient temperature to each well and by removing the PBS by aspiration. PBS 1% BSA solution (2 mL) is added to each well to block non-specific sites and the plates are incubated for 1 hour at 37° C. in $CO_2$ incubator. The blocking solution is removed by aspiration and the wells are washed before adding the cells to the wells.

C. Addition of Cells

Before adding the cells (AC4+/− and AC6−/−) to the prepared plates, they are washed and removed from 10 cm culture dishes by incubating them for 10 minutes at 37° C. in the $CO_2$ incubator with 1.5 mL of Trypsin/EDTA (0.05% Trypsin, 0.53 mM EDTA) (GibcoBRL, Cat: 25300-054) solution. Detached cells are suspended in 5 mL of PBS at ambient temperature, placed in 15 mL conical tubes and centrifuged at 600 g on a clinical centrifuge for 5 minutes. PBS is removed by aspiration, then the cells are counted using a hemacytometer and cell concentration is adjusted to $1 \times 10^6$ cells/mL in DMEM 0.5% BSA.

The cell suspension mixed with a test compound in an amount adequate to provide a range of 25 to 50 µM concentration is incubated for 30 minutes at 37° C. in the $CO_2$ incubator with mixing every ten minutes. An aliquot is retained as a control to determine the basal phosphorylation level before fibronectin-treatment. For fibronectin treatment, 3 mL of the cell suspension is added to the fibronectin matrix in order to obtain 60% confluence ($3 \times 10^6$ cells/well) before incubating for 45 minutes at 37° C. in $CO_2$ incubator. Each sample is performed in duplicate.

At the end of fibronectin stimulation or incubation in suspension, cells are washed with ice-cold PBS supplemented with 1 mM sodium orthovanadate. Cells are lysed directly on the plate by adding 0.5 mL of ice-cold RIPA buffer supplemented with protease inhibitors and 1 mM sodium vanadate. Plates are incubated at 4° C. with frequent agitation for 10 minutes, then disrupted by repeated aspiration with a P1000™ micropipette before transfer to 1.5 mL microcentrifuge tubes. Cellular debris is pelleted at 13,000 rpm (10000 g) for 10 minutes at 4° C. in a microcentrifuge, and supernatants are drawn off into fresh 1.5 mL microcentrifuge tubes.

Protein concentration in the cell lysates is assayed using Bio-Rad Protein concentration kit DC™ (Bio-Rad) according to manufacturer's instructions. Immunoprecipitation of p130$^{cas}$ is performed with an amount of 250 mg protein adjusted in a final volume of 1 mL with RIPA buffer supplemented with 1 mM vanadate and inhibitors.

For the immunoprecipitation, 1 mg (4 mL) of anti-p130$^{cas}$ mouse monoclonal (Transduction Laboratories, Cat: P27820) is added to each sample and the mixture is incubated for 2 hours at 4° C. on a rotating device. As an immunoprecipitation control, the same amount of cell lysate is incubated at this step with 1 mg (3 mL) of rabbit pre-immune serum. Then 20 mL of resuspended Protein G-Agarose™ beads (GibcoBRL, Cat: 15920-010) is added and the mixture is incubated with agitation for 1 hour at 4° C. on a rotating device. Immunoprecipitates are collected by centrifugation at 2000 g for 5 minutes at 4° C. Pellets are washed 3 times with 1 mL of ice-cold RIPA buffer (the supernatant is removed by aspiration). After final wash, the beads are resuspended into 60 mL of SDS sample buffer.

D. SDS-PAGE and Western Blotting

30 µl of immunoprecipitate are separated on a 10% polyacrylamide gel for 1.5 hours at 125V (p130$^{cas}$ is a 130 kDa protein)

Briefly, nitrocellulose membranes are blocked with TBS-Tween (TBST): 20 mM Tris-HCl, pH 7.2-7.4 (BioShop, Cat#: TRS 001)), 150 mM NaCl: (BioShop, Cat#: SOD 001) and 0.1% (v/v) Tween-20: (BioShop, Cat: TWN508) 1% BSA for 1 hour with agitation at ambient temperature. Antiphosphotyrosine monoclonal antibody clone 4G10 (Upstate Biotechnologies) is used at a 1/1000 dilution in TBST 1% BSA and incubated for 1 hour with agitation at ambient temperature. The anti-mouse-IgG-HRP (horseradish peroxidase) conjugate (Jackson Laboratories) is used at a 1/20000 dilution in TBST 1% BSA and incubated for 1 hour at ambient temperature.

E. Data Analysis

The data are analyzed as a function of p130$^{cas}$ phosphorylation status.

Compounds of the invention tested demonstrate a higher level of phosphorylation in the PTPN12−/− cells when compared to the PTPN12+/− cells after fibronectin-treatment. Inhibition of PTPN12 in the +/− cells by a compound of the invention results in a higher phosphorylaton state of p130$^{cas}$ in the treated cells when compared to the non-treated cells.

The foregoing assay is also used, with the appropriate starting reagents and enzyme preparations, to test the ability of the compounds of the invention to inhibit PTPN12 and PTPN1 activity.

EXAMPLE 5

Cell Proliferation

This procedure (Jelinkova, R. B. et al., "Antiproliferative effect of a lectin- and anti-Thy-1.2 antibody-targeted HPMA copolymer-bound doxorubicin on primary and metastatic human colorectal carcinoma and on human colorectal carcinoma transfected with the mouse Thy-1.2 gene", *Bioconjug. Chem.* (2000, September-October), Vol. 11, No. 5, pp. 664-73) is used to assess the effect compounds have on various cell lines with respect to proliferation. The rate of anchorage-independent growth of various tumor cells is quantified by measuring the amount of free isotopic thymidine that has been incorporated into the cells over a period of time. The effect of any compound to inhibit the proliferation of various tumor cells could be used as an indication of its ability to prevent disease progression in cancer.

Cultured tumour cells are harvested cells as per normal procedures: i.e. trypsinize, centrifuge and count cells. A volume of 90 µL is used to seed 5,000 cells/well in a 96 well plate. Cells are incubated for 24 hours at 37° C. under 5% $CO_2$. After incubation, cells should be 80-90% confluent.

$^3$H-thymidine (Amersham) is diluted in cell culture media to a concentration of 100 µCi/mL. The test compound is diluted in the thymidine broth to 10× the final desired concentration.

Then 10 μL of diluted compound is added to the 90 μL of cells already present in the 96-well plates. Six replicates wells are done per treatment in columns 2 to 11. Plates were mixed by rocking.

A known cytotoxic compound such as staurosporine is used in relatively high concentrations as a positive control in column 1. Diluted DMSO is used as a negative control in column 12. The plate is incubated for exactly 24 hours at 37° C.

After incubation, plates are observed under the microscope for obvious cell death, abnormal cell shape, crystal formation of the compound, etc. Then 25 μL volume of cold 50% TCA is added slowly to the 100 μL volume already in each well, and incubated for 1-2 hours at 4° C. The plates are then washed 5× in tap water and allowed to dry completely (usually overnight) at ambient temperature. Finally, 100 μL of scintillation fluid is added to each well and the plates are counted in a Wallac 1450 Microbeta™ counter according to user manual instructions.

The amount of inhibition is determined by the following formula:

% inhibition=100−[(AVG treatment−AVG positive control)/100(AVG negative control−AVG positive control)]

TABLE 3

| Compound | % Inhibition of Proliferation at 50 μM | |
|---|---|---|
| | H460 Cells | PC3 Cells |
| 3-[5-(4-methylbenzylidene)-4-oxo-2-thioxothiazolidin-3-yl]-N-(4-sulfamoylphenyl)-propionamide | 45 | 35 |
| 3-[5-(4-methylbenzylidene)-4-oxo-2-thioxothiazolidin-3-yl]-N-[4-(thiazol-2-ylsulfamoyl)-phenyl]-propionamide | 43 | 47 |

EXAMPLE 6

Cytotoxicity Assay

This procedure is used to assess the effects compounds have on various cell lines with respect to cell viability. Cell viability is quantified using calcein AM (3',6'-Di(O-acetyl)-2',7'-bis[N,N-bis-(carboxymethyl)aminomethyl]-fluorescein, tetraacetoxymethyl ester) and measuring its conversion to a fluorescent product (calcein) with a fluorimeter.

The principle of this assay is based on the presence of ubiquitous intracellular esterase activity found in live cells. By enzymatic reaction of esterase, non-fluorescent cell-permeant calcein AM is converted to the intensely fluorescent calcein. The polyanionic dye calcein is retained within live cells, producing a green fluorescence in live cells. It is a faster, safer, and better-correlated indicator of cytotoxicity than alternative methods (e.g. 3H-Thymidine incorporation). Calcein AM is susceptible to hydrolysis when exposed to moisture, Therefore, prepare aqueous working solutions containing calcein AM immediately prior to use, and used within about one day.

A kit available to do this assay is "LIVE/DEAD® Viability/Cytotoxicity Kit (L-3224)" by Molecular Probes.

Cells were collected from tissue culture flasks and trypsinized, centrifuged, resuspended and counted. Cells were seeded to obtain 80-90% confluence (for normal cells, 10,000 cells/well (8000 cells/well for HUVEC cells)). A cell concentration of 110,000 cells/mL (88,000 cells/well for HUVEC cells) is prepared as 90 μL volume is used per well.

Using an 8-channel multi-dispense pipettor, cells were seeded in the central rows of the plate (Nunclon™ 96 well flat-bottom plate), leaving the peripheral top and bottom rows with same volume of media only. The plates were incubated at 37° C., 5% $CO_2$ overnight for approximately 24 hours.

For test compounds, cell culture media (e.g., RPMI+10% FBS), 10× compound solution of final desired concentration from 20 mM stock compounds was prepared.

10 μl of this 10× compound solution is added to the 90 μL of cells already present in the 96 well plates and a known cytotoxic compound from previous testing is used as a positive control. The negative control is 100% DMSO diluted to the same factor as the compounds.

The plates are incubated at 37° C. for approximately 24 hours, and media is aspirated after plates are spun at 2400 rpm for 10 min at ambient temperature. 100 μL of 1× DPBS (without calcium chloride, without magnesium chloride (GibcoBRL, cat#14190-144)) is added to each well.

The calcein AM solution is prepared by added 50 μg of calcein AM crystal (m.w.=994.87 g/mol, Molecular Probes) and anhydrous DMSO (Sigma Aldrich) to make 1 mM stock and diluting stock to 2× the final desired concentration in 1× DPBS just before the assay. 100 μL of this 2× is added to the 100 μL of DPBS in the wells and the plates are incubated at ambient temperature for 30 minutes. Fluorescence data is read and recorded (Fluoroskan Ascent® FL fluorimeter (excitation~485 nm, emission~527 nm)).

The values for replicates (usually six) are averaged and % inhibition is calculated as follows:

% inhibition=100−[(AVG treatment−AVG positive control)/(AVG negative control−AVG positive control)*100]

TABLE 4

| Compound | % Cytotoxicity On Normal Cells At 50 Mm | | |
|---|---|---|---|
| | HS27 cells | Huvec cells | LL-86 cells |
| 3-[5-(4-methylbenzylidene)-4-oxo-2-thioxothiazolidin-3-yl]-N-(4-sulfamoylphenyl)-propionamide | 0 | 11 | 16 |
| 3-[5-(4-methylbenzylidene)-4-oxo-2-thioxothiazolidin-3-yl]-N-[4-(thiazol-2-ylsulfamoyl)-phenyl]-propionamide | 0 | 42 | 0 |

EXAMPLE 7

In Vivo Tumour Efficacy Study

To test the efficacy of test compounds on H460 subcutaneous xenograft alone and in combination with doxorubicin.

Athymic nude female mice are used for this experiment. A group of 120 mice are inoculated with five million H460 cells in 100 μL Matrigel™ excipient (VWR Canada). Tumours are measured three times a week with digital calipers and the tumour volumes calculated. When tumours have reached an average size of 100 $mm^3$, about three weeks after tumour implantation, the mice are randomized by tumour volume and divided into six groups with 10 mice per group.

Treatments with test compounds continue for about 20 days, and will be oral (gavage), intravenous, subcutaneous, or intraperitoneal depending on the known solubility of the test compound.

The study breakdown in tabular form:

TABLE 5

| Group | Treatment | Dose | Route | Schedule | 2nd Treatment | Dose mg/kg | Route | Schedule |
|---|---|---|---|---|---|---|---|---|
| A | PTE | — | — | — | None | — | — | — |
| B | Compound | 200 mg/kg | Oral | Daily for 20 days | None | — | — | — |
| C | Vehicle | — | Oral | Daily for 20 days | Doxorubicin | 5 | IV | Every 4 days |
| D | Vehicle | — | Oral | Daily for 20 days | Doxorubicin | 7 | IV | Every 4 days |
| E | Compound | 200 mg/kg | Oral | Daily for 20 days | Doxorubicin | 5 | IV | Every 4 days |
| F | Compound | 200 mg/kg | Oral | Daily for 20 days | Doxorubicin | 7 | IV | Every 4 days |

At study termination, the mice are anesthetized 3 hours after the last dose of test compound, and plasma and tissues are harvested and frozen. Tumours are divided into the desired number of aliquots and fast frozen for later analysis.

EXAMPLE 8

Cell Invasion in Matrigel™

This procedure is used to assess the compound effect on the tumor cell invasion through Matrigel™-coated Fluoroblok™ inserts. Invasion allows tumor cells to spread to sites other that the primary tumor. BD Bioscience's BioCoat FluoroBlok™ Invasion Systems™ combine the benefits of the BD BioCoat Matrigel™ Invasion Chambers with the fluorescence blocking membrane capabilities of the BD Falcon™ HTS FluoroBlok™ 24-Multiwell Insert System. The following assay uses this system to assess compound effects on the anti-tumor cell invasion through layer of Matrigel™ extracellular matrix.

The cell lines used are HT 1080 (ATCC, Cat# CCL-121), DU-145 (ATCC, Cat# HTB-81), PC3 (ATCC, Cat# CRL-1435) or B16F1 (ATCC, Cat# CRL-6323).

The invasion test system is removed from the package from −20° C. storage and allowed to warm to ambient temperature. PBS is added to the interior of the inserts and they are allowed to rehydrate for 2 hours at 37° C. Then the medium is removed and 450 µL cell suspensions of tumour cells (grown to 50-70% confluence, trypsinized, and resuspended in medium without serum at $1 \times 10^6$/mL) is added to the top chamber. Test compounds are added to the top chamber at 10× the desired final concentration in 50 µL volumes. DMSO acts as control.

Then 750 µL of medium containing 50% fresh growth medium with 10% FBS and 50% NIH 3T3-conditioned medium is added to each of the bottom wells. The invasion system is then incubated for 24 to 48 hours at 37° C., in a 5% $CO_2$ atmosphere.

Following incubation, the insert plate is transferred into a second 24-well plate containing 0.5 mL of 5 µg/mL calcein AM (Molecular Probes) in Hanks buffered salt solution (HBSS), and plates are incubated for 1 hour at 37° C., 5% $CO_2$.

Fluorescence data indicating cell invasion is read in a Fluoroskan Ascent FL™ (LabSystems) with bottom reading at excitation/emission wavelength of 485/538 nm.

Data is expressed as fluorescence unit (FU) from the sum of middle 25 areas per 24-well or as percentage of invasion inhibition by following formula: % of invasion inhibition=100−FU of compound treated cell invasion/FU of DMSO treated cell invasion times 100.

The compounds inhibit invasion in this assay, and thus may be used to prevent metastasis in cancer and tissue remodeling.

EXAMPLE 9

Peritoneal Macrophage Stimulation and Analysis

A. Establishment of Inflammation Assay Panel

Macrophages are important elements of innate immunity to infection and are among the first cell type in the immune response to be exposed to and activated by infectious agents. IFN-γ and LPS are potent activators of macrophages, priming them for a variety of biological effects. IFN-γ, initially secreted by NK and T cells in response to infection, converts macrophages from a resting to an activated state (inflammatory macrophages), priming them for antimicrobial activity manifested by increased killing of intracellular pathogens, and antigen processing and presentation to lymphocytes. The action of IFN-γ is synergized with the LPS second messenger, enhancing the stimulation of macrophages through the activation of NF-κB, that results in the transcriptional up-regulation of a number of genes involved in the cell-mediated immune response, including inducible iNOS (nitric oxide synthase). Activated macrophages are qualitatively different from quiescent macrophages. These differences are typically observed by an increased proliferation index, up-regulated expression of MHC-II, and production of various bioactive molecules. The latter biological effects are mediated by NO (nitric oxide) release and increased production of pro-inflammatory cytokines (IL-6, TNF-γ, IL-1). Primary macrophages derived from Balb/c mice and RAW 264.7 cells (Balb/c background) were used to establish in vitro inflammatory models with fast and reliable readouts.

B. Materials and Methods

1. Reagents

The iNOS inhibitor NG-monomethyl-L-arginine (L-NMMA) and murine rIFN-γ are purchased from Calbiochem, (San Diego, Calif.). Protein-free, phenol/water-extracted LPS (from E. coli serotype 0111:B4 0127:B8), Zymosan A™, dexamethasone and hydrocortisone, sulfanilamide and N-(1-naphthyl)-ethylenediamine, arare purchased from Sigma (St. Louis, Mo.). Human recombinant vascular endothelial growth factor (VEGF) is purchased from R&D Systems (Minneapolis, Minn.). Rabbit polyclonal antibody against active (phosphorylated) extracellular signal-regulated kinase (ERK), as well as HRP-conjugated donkey anti-rabbit IgG are obtained from Promega (Madison, Wis.). ELISA dual-set kit for detection of IL-6 is purchased from PharMingen (San Diego, Calif.). Anti-murine iNOS/NOS type II and cyclooxygenase-2 (COX-2) antibodies are obtained from Transduction Laboratories (Lexington, Ky.).

Female BALB/c inbred mice, 6-12 weeks of age, are purchased from Harlan Inc. (Indianapolis, Ind.) and housed under fluorescent light for 12 h per day. Mice are housed in cages, and maintained in compliance with the Canadian Council on Animal Care standards.

2. Isolation of Primary Mouse Macrophages

Peritoneal exudate macrophages are isolated by peritoneal lavage with ice-cold sterile physiological saline 24 hours after intraperitoneal injection of BALB/c mice with 0.5 mL of sterile Zymosan A™ (1 mg/0.5 mL 0.9% saline). Cells are washed and resuspended in RPMI 1640 supplemented with 1 mM D-glucose, 1 mM sodium pyruvate, 100 units/mL penicillin, 100 µg/mL streptomycin, and 5% FBS.

3. Treatment of Primary Macrophages

Primary macrophages (1.5×105 cells/well) are grown in 96-well plates (nitrite assay), or 6-well plates (2×106 cells/well) for measurement of iNOS and COX-2 expression. Following 3 hours incubation, at 37° C., 5% $CO_2$ (allowing macrophages to attach) cells are stimulated with LPS (5 µg/mL) and IFN-γ (100 U/mL) in the absence or presence of various concentrations of test compounds (all treatments are replicated six times). Cells are incubated for an additional 24 hours, and cell free culture supernatants from each well are collected for NO and cytokine determination. The remaining cells are stained with crystal violet or MTS to determine effect of the test compounds on cell survival.

4. NO Production

Following stimulation, the production of NO is determined by assaying culture supernatants for $NO_2$, a stable reaction product of NO with molecular oxygen. Briefly, 100 µL of culture supernatant is reacted with an equal volume of Griess reagent at ambient temperature for 10 minutes. The absorbance at 550 nm is determined. All measurements are performed six times. The concentration of $NO_2$ is calculated based on comparison with a standard curve prepared using $NaNO_2$.

5. Western Blot Analysis

After incubation with the indicated stimuli in the presence of inhibitors, cells (duplicate samples, 2×10$^6$ cell/6-wells plate) are washed in PBS and lysed on ice in 60 µL of lysis buffer. The protein content of each sample is determined using the Bradford protein assay kit (Bio-Rad, Richmond, Calif.). Absorbance is measured at 750 nm with a Beckman DU530 spectrophotometer (Palo Alto, Calif.). Proteins are mixed with 45×SDS sample buffer. Following separation of proteins by SDS-PAGE, using 8% bis-acrylamide in the separation gel, the proteins are transferred from the gels onto PVDF membranes using a MiniProtean™ III Cell (Bio-Rad), at 100 V for 1.5 hours. Equal amounts of protein (5 µg) are loaded onto SDS-PAGE gels and examined by Western blot analysis with anti-actin, anti-iNOS, anti-COX-2 murine monoclonal antibodies, according to the manufacturer's specifications (Transduction Laboratories). Primary antibodies, in 5% blocking buffer (5% NFM/TTBS), are incubated with blots 2 hours or overnight at 4° C., followed by incubation with peroxidase-conjugated secondary antibody. Chemiluminescence substrates are used to reveal positive bands. The bands are exposed on X-ray films. The films are used to analyze the impact of inhibitors on expression of iNOS and COX-2 compared to various controls and "house-keeping" protein (Actin) concentration to control the protein loading and detect any non-specific effects on protein production. The Multi-Analyst™/PC system from Biorad is used to quantitate the bands of the expressed protein on the film. This version of Multi-Analyst is used with the Bio-Rad Gel Doc 1000™ imaging system. White light is chosen as the selected light source, thus the signal strength is measured in OD (optic density) units. The OD of each band is being subtracted to a global background area of the gel.

C. In Vitro Angiogenesis

HUVEC cells cultured for 24 hours in M199 with 0.5% FCS are plated at 6×105 cells/well in 12-well plates pre-coated with 300 µL of Matrigel (10.7 mg/mL; Becton Dickinson) in M199 with 0.5% FCS in the presence of VEGF (1 ng/mL), and in the absence or presence of positive control (Z)-3-[2,4-dimethyl-5-(2-oxo-1,2-dihydroindol-3-ylidenemethyl)-1H-pyrrol-3-yl]propionic acid or various inhibitors. After 5 hours of incubation in a 5% $CO_2$-humidified atmosphere at 37° C., the three-dimensional organization of the cells is examined using an inverted photomicroscope. The cells are fixed with crystal violet (0.05% in 20% ethanol) and digitally photographed.

D. Enzyme Immunoassays for Mouse IL-6

IL-6 levels are determined with PharMingen's OptEIA™ ELISA set developed using an anti-mouse IL-6 Ab pair and mouse rIL-6 standard (PharMingen). Maxisorp F16™ multiwell strips (Nunc, Roskilde, Denmark) are coated with anti-mouse IL-6 capture Ab (at recommended concentration) in 0.1 M $NaHCO_3$, pH 9.5, 100 µL/well, overnight at 4° C. Plates are washed three times with 0.05% Tween 20 in PBS (PBST) and blocked for 1 hour at ambient temperature with 200 µL/well of 10% FCS in PBS (blocking and dilution buffer). Plates are washed three times with PBST and duplicate samples (100 µL/well) or standards (100 µL/well) in diluent buffer are incubated for 2 hours at ambient temperature. Plates are washed five times with PBST and incubated with biotinylated anti-mouse IL-6 and avidin-horseradish peroxidase conjugate (at concentrations recommended by the manufacturer) for 1 hour at ambient temperature. Plates are washed seven times with PBST and 100 µL of 3,3'5,5' tetramethylbenzidine substrate solution (TMB substrate reagent set, BD PharMingen) is added to each well. After 15-30 minute incubation at ambient temperature, color development is terminated by adding 50 µL of 2N $H_2SO_4$ (Sigma). Absorbance is read at 450 nm with an EL 312e™ microplate reader or the like. The lower limit of detection for IL-6 is 15.6 µg/mL.

EXAMPLE 10

NIDDM Model

In vivo oral treatment with pharmaceuticals compositions of the invention result in significant glucose lowering in several rodent models of diabetes. In db/db mice, oral administration of the compounds elicited significant correction of hyperglycemia. In a streptozotocin-induced diabetic mouse model, compounds potentiate the glucose-lowering effect of insulin.

In normal rats, compounds improve oral glucose tolerance with significant reduction in insulin release following glucose challenge. A structurally related inactive analog is not effective on insulin receptor activation or glucose lowering in db/db mice.

What is claimed is:

1. A pharmaceutical composition comprises a pharmaceutically acceptable carrier, diluent or excipient and a compound of formula (Ia):

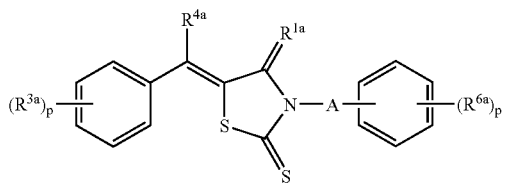

(Ia)

wherein:

each p is independently 1 to 5;

A is linker of four atoms and is selected from the group consisting of an optionally substituted straight or branched alkylene chain of four carbons, an optionally substituted straight or branched alkenylene chain of four carbons, $-R^{8a}-C(R^{2a})-N(R^{5a})-$, $-R^{8a}-N(R^{5a})-C(R^{2a})-$, $-R^{8a}-O-C(R^{2a})-$, $-R^{7a}-O-C(R^{2a})-R^{7a}-$, $-R^{8a}-O-R^{7a}-$, $-R^{7a}-C(R^{2a})-N(R^{5a})-S(O)_t-$ (where t is 0 to 2), $-R^{8a}-N(R^{5a})-R^{7a}-$, $-R^{8a}-S(O)_t-R^{7a}-$ (where t is 0 to 2), $-R^{9a}-N(R^{5a})-$, $-R^{9a}-O-$, and $-R^{9a}-C(R^{2a})-$;

$R^{1a}$ and $R^{2a}$ are each independently $=O$ or $=S$;

$R^{3a}$ is alkyl, alkenyl, aryl, aralkyl, aralkenyl, cycloalkyl, cycloalkylalkyl, chloro, iodo, bromo, haloalkyl, haloalkoxy, nitro, cyano, $-N=N-O-R^{11a}$, $-OR^{10a}$, $-C(O)OR^{10a}$, $-C(O)N(R^{10a})_2$, $-N(R^{12a})_2$, $-N(R^{10a})C(O)R^{10a}$, $-N(R^{10a})C(O)OR^{11a}$, $-S(O)_t R^{10a}$ (where t is 0 to 2), $-S(O)_t N(R^{10a})_2$ (where t is 0 to 2), or heterocyclylalkyl;

$R^{4a}$ is hydrogen, alkyl, aralkyl, aryl, haloalkyl, cycloalkyl, cycloalkylalkyl, heterocyclyl or heterocyclylalkyl;

$R^{5a}$ is hydrogen, alkyl, aralkyl, or aryl;

$R^{6a}$ is alkenyl, aryl, aralkyl, aralkenyl, cycloalkyl, cycloalkylalkyl, haloalkyl, haloalkoxy, nitro, cyano, $-N=N-O-R^{11a}$, $-C(O)N(R^{10a})_2$, $-N(R^{10a})_2$, $-N(R^{10a})C(O)R^{10a}$, $-N(R^{10a})C(O)OR^{11a}$, $-S(O)_t R^{10a}$ (where t is 0 to 2), $-S(O)_t N(R^{10a})_2$ (where t is 0 to 2), $-S(O)_t NH-R^{14a}$, heterocyclyl or heterocyclylalkyl;

each $R^{7a}$ is an optionally substituted alkylene chain of one carbon;

each $R^{8a}$ is an optionally substituted straight or branched alkylene or alkenylene chain of two carbons;

each $R^{9a}$ is an optionally substituted alkylene chain of three carbons;

each $R^{10a}$ is hydrogen, alkyl, alkenyl, cycloalkyl, cycloalkylalkyl, aralkyl or aryl;

$R^{11a}$ is hydrogen, alkyl or aralkyl;

$R^{12a}$ is hydrogen, aryl or aralkyl; and $R^{14a}$ is a thiazole;

as a single stereoisomer, a mixture of stereoisomers, or as a racemic mixture of stereoisomers; or as a solvate or polymorph; or as a pharmaceutically acceptable salt thereof.

2. The pharmaceutical composition of claim 1 wherein the compound of formula (Ia) is a compound of formula (Ia) wherein:

A is $-R^{8a}-C(R^{2a})-N(R^{5a})-$;

$R^{1a}$ and $R^{2a}$ are each independently =O or =S;

$R^{3a}$ is alkyl, aryl, aralkyl, chloro, iodo, bromo, haloalkyl, haloalkoxy, nitro, cyano, $-N=N-O-R^{11a}$, $-OR^{12a}$, $-C(O)OR^{10a}$, $-C(O)N(R^{10a})_2$, $-N(R^{12a})_2$, $-N(R^{10a})C(O)R^{10a}$, $-N(R^{10a})C(O)OR^{11a}$, $-S(O)_t R^{10a}$ (where t is 0 to 2), or $-S(O)_t N(R^{10a})_2$ (where t is 0 to 2);

$R^{4a}$ is hydrogen or alkyl;

$R^{5a}$ is hydrogen or alkyl;

$R^{6a}$ is aryl, aralkyl, haloalkyl, haloalkoxy, nitro, cyano, $-N=N-O-R^{11a}$, $-C(O)N(R^{10a})_2$, $-N(R^{10a})_2$, $-N(R^{10a})C(O)R^{10a}$, $-N(R^{10a})C(O)OR^{11a}$, $-S(O)_t R^{10a}$ (where t is 0 to 2), $-S(O)_t NH-R^{14a}$ or $-S(O)_t N(R^{10a})_2$ (where t is 0 to 2);

each $R^{8a}$ is an optionally substituted straight or branched alkylene or alkenylene chain of two carbons;

each $R^{10a}$ is hydrogen, alkyl, aralkyl or aryl;

$R^{11a}$ is hydrogen, alkyl or aralkyl;

$R^{12a}$ is hydrogen, aryl or aralkyl; and $R^{14a}$ is a thiazole.

3. The pharmaceutical composition of claim 2 wherein the compound of formula (Ia) is a compound of formula (Ia) wherein:

A is $-R^{8a}-C(R^{2a})-N(R^{5a})-$;

$R^{1a}$ and $R^{2a}$ are each independently =O or =S;

$R^{3a}$ is alkyl, aryl, aralkyl, chloro, iodo, bromo, haloalkyl, or haloalkoxy;

$R^{4a}$ is hydrogen or alkyl;

$R^{5a}$ is hydrogen or alkyl;

$R^{6a}$ is $-C(O)N(R^{10a})_2$, $-S(O)_t R^{10a}$ (where t is 0 to 2), $-S(O)_t NH-R^{14a}$ or $-S(O)_t N(R^{10a})_2$ (where t is 0 to 2);

each $R^{8a}$ is an optionally substituted straight or branched alkylene or alkenylene chain of two carbons;

$R^{14a}$ is a thiazole; and each $R^{10a}$ is hydrogen, alkyl, aralkyl or aryl.

4. The pharmaceutical composition of claim 3 wherein the compound of formula (Ia) is a compound of formula (Ia) wherein:

A is $-R^{8a}-C(R^{2a})-N(R^{5a})-$;

$R^{1a}$ and $R^{2a}$ are both =O;

$R^{3a}$ is alkyl, haloalkyl or haloalkoxy;

$R^{4a}$ is hydrogen;

$R^{5a}$ is hydrogen or alkyl;

$R^{6a}$ is $-S(O)_2 N(R^{10a})_2$;

$R^{8a}$ is ethylene; and each $R^{10a}$ is hydrogen or alkyl.

5. A pharmaceutical composition comprising a pharmaceutically acceptable carrier, diluent or excipient and a compound selected from the group consisting of:

3-[5-(4-methylbenzylidene)-4-oxo-2-thioxothiazolidin-3-yl]-N-(4-sulfamoylphenyl)-propionamide; and 3-[5-(4-methylbenzylidene)-4-oxo-2-thioxothiazolidin-3-yl]-N-[4-(thiazol-2-ylsulfamoyl)-phenyl]-propionamide.

6. A pharmaceutical composition useful in inhibiting signalling pathways mediated by PTPN12, PTPN2 or PTPN1 comprising a pharmaceutically acceptable carrier, diluent or excipient and a compound of formula (Ia):

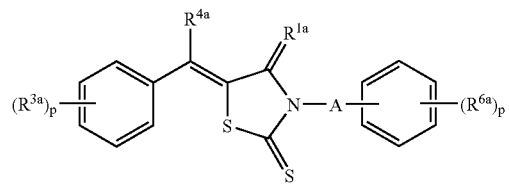

(Ia)

wherein:

each p is independently 1 to 5;

A is linker of four atoms and is selected from the group consisting of an optionally substituted straight or branched alkylene chain of four carbons, an optionally substituted straight or branched alkenylene chain of four carbons, $-R^{8a}-C(R^{2a})-N(R^{5a})-$, $-R^{8a}-N(R^{5a})-C(R^{2a})-$, $-R^{8a}-O-C(R^{2a})-$, $-R^{7a}-O-C(R^{2a})-R^{7a}-$, $-R^{8a}-O-R^{7a}-$, $-R^{7a}-C(R^{2a})-N(R^{5a})-S(O)_t-$ (where t is 0 to 2), $-R^{8a}-N(R^{5a})-R^{7a}-$, $-R^{8a}-S(O)_t-R^{7a}-$ (where t is 0 to 2), $-R^{9a}-N(R^{5a})-$, $-R^{9a}-O-$, and $-R^{9a}-C(R^{2a})-$;

$R^{1a}$ and $R^{2a}$ are each independently =O or =S;

$R^{3a}$ is alkyl, alkenyl, aryl, aralkyl, aralkenyl, cycloalkyl, cycloalkylalkyl, chloro, iodo, bromo, haloalkyl, haloalkoxy, nitro, cyano, $-N=N-O-R^{11a}$, $-OR^{12a}$, $-C(O)OR^{10a}$, $-C(O)N(R^{10a})_2$, $-N(R^{12a})_2$, $-N(R^{10a})C(O)R^{10a}$, $-N(R^{10a})C(O)OR^{11a}$, $-S(O)_t R^{10a}$ (where t is 0 to 2), $-S(O)_t N(R^{10a})_2$ (where t is 0 to 2), or heterocyclylalkyl;

$R^{4a}$ is hydrogen, alkyl, aralkyl, aryl, haloalkyl, cycloalkyl, cycloalkylalkyl, heterocyclyl or heterocyclylalkyl;

$R^{5a}$ is hydrogen, alkyl, aralkyl, or aryl;

$R^{6a}$ is alkenyl, aryl, aralkyl, aralkenyl, cycloalkyl, cycloalkylalkyl, haloalkyl, haloalkoxy, nitro, cyano, $-N=N-O-R^{11a}$, $-C(O)N(R^{10a})_2$, $-N(R^{10a})_2$, $-N(R^{10a})C(O)R^{10a}$, $-N(R^{10a})C(O)OR^{11a}$, $-S(O)_t R^{10a}$ (where t is 0 to 2), $-S(O)_t N(R^{10a})_2$ (where t is 0 to 2), $-S(O)_t NH-R^{14a}$, heterocyclyl or heterocyclylalkyl;

each $R^{7a}$ is an optionally substituted alkylene chain of one carbon;

each $R^{8a}$ is an optionally substituted straight or branched alkylene or alkenylene chain of two carbons;

each $R^{9a}$ is an optionally substituted alkylene chain of three carbons;

each $R^{10a}$ is hydrogen, alkyl, alkenyl, cycloalkyl, cycloalkylalkyl, aralkyl or aryl;

$R^{11a}$ is hydrogen, alkyl or aralkyl;

$R^{12a}$ is hydrogen, aryl or aralkyl; and $R^{14a}$ is a thiazole;

as a single stereoisomer, a mixture of stereoisomers, or as a racemic mixture of stereoisomers; or as a solvate or polymorph; or as a pharmaceutically acceptable salt thereof.

* * * * *

SEQUENCE LISTING

```
<160> NUMBER OF SEQ ID NOS: 2

<210> SEQ ID NO 1
<211> LENGTH: 9
<212> TYPE: PRT
<213> ORGANISM: Unknown
<220> FEATURE:
<223> OTHER INFORMATION: Signature sequence of conserved catalytic
      domain of protein tyrosine phosphatases (PTPs)
<220> FEATURE:
<221> NAME/KEY: MISC_FEATURE
<222> LOCATION: (1)..(1)
<223> OTHER INFORMATION: Xaa = Isoleucine or Valine
<220> FEATURE:
<221> NAME/KEY: MISC_FEATURE
<222> LOCATION: (4)..(5)
<223> OTHER INFORMATION: Xaa = any amino acid
<220> FEATURE:
<221> NAME/KEY: MISC_FEATURE
<222> LOCATION: (7)..(8)
<223> OTHER INFORMATION: Xaa = any amino acid
<220> FEATURE:
<221> NAME/KEY: MISC_FEATURE
<222> LOCATION: (9)..(9)
<223> OTHER INFORMATION: Xaa = Serine or Threonine

<400> SEQUENCE: 1

Xaa His Cys Xaa Xaa Gly Xaa Xaa Xaa
1               5

<210> SEQ ID NO 2
<211> LENGTH: 13
<212> TYPE: PRT
<213> ORGANISM: Artificial Sequence
<220> FEATURE:
<223> OTHER INFORMATION: Synthesized substrate peptide
<220> FEATURE:
<221> NAME/KEY: MOD_RES
<222> LOCATION: (7)..(7)
<223> OTHER INFORMATION: PHOSPHORYLATION

<400> SEQUENCE: 2

Thr Ser Thr Glu Pro Gln Tyr Gln Pro Gly Glu Asn Leu
1               5                   10
```